US007816400B2

(12) United States Patent
Li et al.

(10) Patent No.: US 7,816,400 B2
(45) Date of Patent: Oct. 19, 2010

(54) USE OF ACACETIN AND RELATED COMPOUNDS AS POTASSIUM CHANNEL INHIBITORS

(75) Inventors: Gui-Rong Li, Hong Kong (CN); Chu-Pak Lau, Hong Kong (CN); Guo-Wei Qin, Shanghai (CN); Hong-Bing Wang, Shanghai (CN)

(73) Assignees: The University of Hong Kong, Hong Kong (CN); Shanghai Institute of Materia Medica, Chinese Academy of Sciences, Shanghai (CN)

( * ) Notice: Subject to any disclaimer, the term of this patent is extended or adjusted under 35 U.S.C. 154(b) by 70 days.

(21) Appl. No.: 12/039,921

(22) Filed: Feb. 29, 2008

(65) Prior Publication Data
US 2008/0214493 A1 Sep. 4, 2008

Related U.S. Application Data

(60) Provisional application No. 60/892,556, filed on Mar. 2, 2007.

(51) Int. Cl.
*A61K 31/352* (2006.01)
*A61P 9/06* (2006.01)
(52) U.S. Cl. .................................. 514/456
(58) Field of Classification Search .............. None
See application file for complete search history.

(56) References Cited

U.S. PATENT DOCUMENTS

2004/0087516 A1* 5/2004 Rosenbloom ............... 514/27

OTHER PUBLICATIONS

Lekakis, J. et al., European Journal of Cardiovascular Prevention & Rehabilitation, Polyphenolic compounds from red grapes acutely improve endothelial function in patients with coronary heart disease, vol. 12, issue 6, pp. 596-600 (Dec. 2005).*
Wallace, C.H.R. et al., British Journal of Pharmacology, Inhibition of cardiac voltage-gated sodium channels by grape polyphenols, vol. 149, pp. 657-665 (2006).*
Brundel et al., Journal of the American College of Cardiology, Alterations in Potassium Channel Gene Expression in Atria of Patients with Persistent and Paroxysmal Atrial Fibrillation: Differential Regulation of Protein and mRNA Levels for K+ Channels, vol. 37, issue 3, pp. 926-932 (2001).*
Calderone, V. et al., Naunyn-Schmiedeberg's Arch Pharmacol, Vasorelaxing effects of flavonoids: investigation on the possible involvement of potassium channels, vol. 370, pp. 290-298 (2004).*
Merriam Webster Online Dictionary "derivative"; also available at http://www.merriam-webster.com/dictionary/derivative.*
Merriam Webster Online Dictionary "analogue"; also available at http://www.merriam-webster.com/dictionary/analogue.*
Merriam Webster Online Dictionary "glycoside"; also available at http://www.merriam-webster.com/dictionary/glycoside.*
MayoClinic.com "cardiac arrhythmia"; also available at http://www.mayoclinic.com/health/heart-arrhythmias; last viewed Feb. 2, 2010.*
Calderone, V. et al., Naunyn-Schmiedeberg's Arch Pharmacol: "Vasorelaxing effects of flavonoids: invetigation on the possible involvement of potassium channels", vol. 370, pp. 290-298 (2004).*
Benjamin, Emelia J. et al., "Impact of Atrial Fibrillation on the Risk of Death: The Framingham Heart Study," *Circulation: Journal of the American Heart Association*, 1998, vol. 98, pp. 946-952.
Blaauw, Y. et al., "Early' Class III Drugs for the Treatment of Atrial Fibrillation: Efficacy and Atrial Selectivity of AVE0118 in Remodeled Atria of the Goat," *Circulation: Journal of the American Heart Association*, 2004, vol. 110, pp. 1717-1724.
Bosch, Ralph F. et al., "Ionic mechanisms of electrical remodeling in human atrial fibrillation," *Cardiovascular Research*, 1999, vol. 44, pp. 121-131.
Burashnikov, Alexander et al., "Atrium-Selective Sodium Channel Block as a Strategy for Suppression of Atrial Fibrillation: Differences in Sodium Channel Inactivation Between Atria and Ventricles and the Role of Ranolazine," *Circulation: Journal of the American Heart Association*, 2007, vol. 116, pp. 1449-1457.
Cahill, Sean A. et al., "Propafenone and Its Metabolites Preferentially Inhibit $I_{Kr}$ in Rabbit Ventricular Myocytes," *The Journal of Pharmacology and Experimental Therapeutics*, 2004, vol. 308, No. 1, pp. 59-65.
Chiou, Chuen-Wang et al., "Efferent Vagal Innervation of the Canine Atria and Sinus and Atrioventricular Nodes," *Circulation: Journal of the American Heart Association*, 1997, vol. 95, p. 2573-2584.
Courtemanche, Marc et al., "Ionic targets for drug therapy and atrial fibrillation-induced electrical remodeling: insights from a mathematical model," *Cardiovascular Research*, 1999, vol. 42, pp. 477-489.
D'Aloia, Antonio D. et al., "Sustained torsade de pointes occurring early during oral sotalol therapy for atrial fibrillation recurrence prophylaxis in a patient without heart disease," *International Journal of Cardiology*, 2005, vol. 105, pp. 337-339.
De Haan, Sunniva et al., "AVE0118, Blocker of the Transient Outward Current (Ito) and Ultrarapid Delayed Rectifier Current (IKur), Fully Restores Atrial Contractility After Cardioversion of Atrial Fibrillation in the Goat," *Circulation: Journal of the American Heart Association*, 2006, vol. 114, pp. 1234-1242.
Dong, Ming-Qing et al., "Characterization of Recombinant Human Cardiac *KCNQ1/KCNE1* Channels ($I_{Ks}$) Stably Expressed in HEK 293 Cells," *Journal of Membrane Biology*, 2006, vol. 210, pp. 183-192.
Doostdar, Hamed et al., "Bioflavonoids: selective substrates and inhibitors for cytochrome P450 CYP1A and CYP1B1," *Toxicology*, 2000, vol. 144, pp. 31-38.
Fedida, David et al., "Identity of a Novel Delayed Rectifier Current From Human Heart With a Cloned K+ Channel Current," *Circulation Research*, Jul. 1993, vol. 73, No. 1, pp. 210-215.

(Continued)

*Primary Examiner*—Shaojia Anna Jiang
*Assistant Examiner*—Bahar Schmidtmann
(74) *Attorney, Agent, or Firm*—Saliwanchik, Lloyd & Saliwanchik

(57) ABSTRACT

This invention provides a method for treating or preventing human atrial arrhythmia (fibrillation) using the leading flavone compound acacetin, and its derivatives and analogues that inhibit the ultra-rapidly-activating delayed rectifier potassium current ($I_{Kur}$ or $I_{Ksus}$), transient outward potassium ($I_{to}$), and acetylcholine-activated potassium current ($I_{K.ACh}$).

10 Claims, 13 Drawing Sheets

OTHER PUBLICATIONS

Gao, Zhan et al., "Inhibition of ultra-rapid delayed rectifier K+ current by verapamil in human atrial myocytes," *Journal of Molecular and Cellular Cardiology*, 2004, vol. 36, pp. 257-263.

Gögelein, Heinz et al., "Effects of the atrial antiarrhythmic drug AVE0118 on cardiac ion channels," *Naunyn-Schmiedeberg's Arch. Pharmacol.*, 2004, vol. 370, pp. 183-192.

Hashimoto, Norio et al., "Tertiapin, a selective $IK_{ACh}$ blocker, terminates atrial fibrillation with selective atrial effective refractory period prolongation," *Pharmacological Research*, 2006, vol. 54, pp. 136-141.

Hsu, Ya-Ling et al., "Acacetin inhibits the proliferation of Hep G2 by blocking cell cycle progression and inducing apoptosis," *Biochemical Pharmacology*, 2004, vol. 67, pp. 823-829.

Kawaii, Satoru et al., "Quantitative Study of Flavonoids in Leaves of Citrus Plants," *Journal of Agricultural Food Chemistry*, 2000, vol. 48, pp. 3865-3871.

Kim, Young M. et al, "A Myocardial Nox2 Containing NAD(P)H Oxidase Contributes to Oxidative Stress in Human Atrial Fibrillation,"*Ciruclation Research: The Journal of the American Heart Association*, 2005, vol. 97, pp. 629-636.

Kraft, Carola et al., "In Vitro Antiplasmodial Evaluation of Medicinal Plants from Zimbabwe," *Phytotherapy Research*, 2003, vol. 17, pp. 123-128.

Li, Gui-Rong et al., "Adrenergic Modulation of Ultrarapid Delayed Rectifier K+ Current in Human Atrial Myocytes," *Circulation Research*, 1996, vol. 78, pp. 903-915.

Li, Gui-Rong et al., "Biphasic effects of cell vol. on excitation-contraction coupling in rabbit ventricular myocytes," *American Journal of Physiological Heart Circulation Physiology*, 2002, vol. 282, pp. H1270-H1277.

Li, Gui-Rong et al., "Evidence for Two Components of Delayed Rectifier K+ Current in Human Ventricular Myocytes," *Circulation Research*, 1996, vol. 78, pp. 689-696.

Li, Gui-Rong et al., "Heterogeneity of Sodium Current in Atrial vs Epicardial Ventricular Myocytes of Adult Guinea Pig Hearts," *Journal of Molecular Cell Cardiology*, 2002, vol. 34, pp. 1185-1194.

Liao, Yong-Hong et al., "Novel and Known Constituents from *Buddleja* Species and Their Activity against Leukocyte Eicosanoid Generation," *Journal of Natural Products*, 1999, vol. 62, pp. 1241-1245.

Lip, Gregory Y.H. et al., "Management of atrial fibrillation," *Lancet*, 2007, vol. 370, pp. 604-618.

Lloyd-Jones, Donald M. et al., "Lifetime Risk for Development of Atrial Fibrillation: The Framingham Heart Study," *Circulation: The Journal of the American Heart Association*, 2004, vol. 110, pp. 1042-1046.

Mihm, Michael J. et al., "Impaired Myofibrillar Energetics and Oxidative Injury During Human Atrial Fibrillation," *Circulation: The Journal of the American Heart Association*, 2001, vol. 104, pp. 174-180.

Milberg, Peter et al., "Comparison of the In Vitro Electrophysiologic and Proarrhythmic Effects of Amiodarone and Sotalol in a Rabbit Model of Acute Atrioventricular Block," *Journal of Cardiovascular Pharmacology*, 2004, vol. 44, pp. 278-286.

Nattel, Stanley et al., "New Approaches to Atrial Fibrillation Management: A Critical Review of a Rapidly Evolving Field," *Drugs*, 2002, vol. 62, No. 16, pp. 2377-2397.

Pan, Min-Hsiung et al., "Acacetin suppressed LPS-induced up-expression of iNOS and COX-2 in murine macrophages and TPA-induced tumor promotion in mice," *Biochemical Pharmacology*, 2006, vol. 72, pp. 1293-1303.

Peukert, Stefan et al., "Identification, Synthesis, and Activity of Novel Blockers of the Voltage-Gated Potassium Channel Kv1.5," *Journal of Medicinal Chemistry*, 2003, vol. 46, pp. 486-498.

Pirard, Bernard et al., "The Discovery of Kv1.5 Blockers as a Case Study for the Application of Virtual Screening Approaches," *Journal of Chemical Information and Modeling*, 2005, vol. 45, pp. 477-485.

Regan, Christopher P. et al., "In Vivo Cardiac Electrophysiologic Effects of a Novel Diphenylphosphine Oxide $I_{Kur}$ Blocker, (2-Isopropyl-5-methylcyclohexyl) Diphenylphosphine Oxide, in Rat and Nonhuman Primate," *The Journal of Pharmacology and Experimental Therapeutics*, 2006, vol. 316, No. 2, pp. 727-732.

Schauerte, Patrick et al., "Catheter Ablation of Cardiac Autonomic Nerves for Prevention of Vagal Atrial Fibrillation," *Circulation: The Journal of the American Heart Association*, 2000, vol. 102, pp. 2774-2780.

Seki, Akiko et al., "Effects of NIP-141 on K Currents in Human Atrial Myocytes," *Journal of Cardiovascular Pharmacology*, 2002, vol. 39, pp. 29-38.

Shi, Hong et al., "Differential Alterations of Receptor Densities of Three Muscarinic Acetylcholine Receptor Subtypes and Current Densities of the Corresponding K+ Channels in Canine Atria with Atrial Fibrillation Induced by Experimental Congestive Heart Failure," *Cellular Physiology and Biochemistry*, 2004, vol, 14, pp. 31-40.

Singh, Rana P. et al., "Acacetin inhibits cell growth and cell cycle progression, and induces apoptosis in human prostate cancer cells: structure-activity relationship with linarin and linarin acetate," *Carcinogenesis*, 2005, vol. 26, No. 4, pp. 845-854.

Tang, Qiang et al., "The membrane permeable calcium chelator BAPTA-AM directly blocks human ether a-go-go-related gene potassium channels stably expressed in HEK 293 cells," *Biochemical Pharmacology*, 2007, vol. 74, pp. 1596-1607.

Tian, Miao et al., "Effects of the antifungal antibiotic clotrimazole on human cardiac repolarization potassium currents," *British Journal of Pharmacology*, 2006, vol. 147, pp. 289-297.

Wang, Thomas J. et al., "Temporal Relations of Atrial Fibrillation and Congestive Heart Failure and Their Joint Influence on Mortality: The Framingham Heart Study," *Circulation: The Journal of the American Heart Association*, 2003, vol. 107, pp. 2920-2925.

Wang, Zhiguo et al., "Rapid and slow components of delayed rectifier current in human atrial myocytes," *Circulation Research*, 1994, vol. 28, No. 6, pp. 1540-1546.

Zhang, Kai et al., "Inhibition of Glutathione Reductase by Plant Polyphenols," *Biochemical Pharmacology*, 1997, vol. 54, pp. 1047-1053.

\* cited by examiner

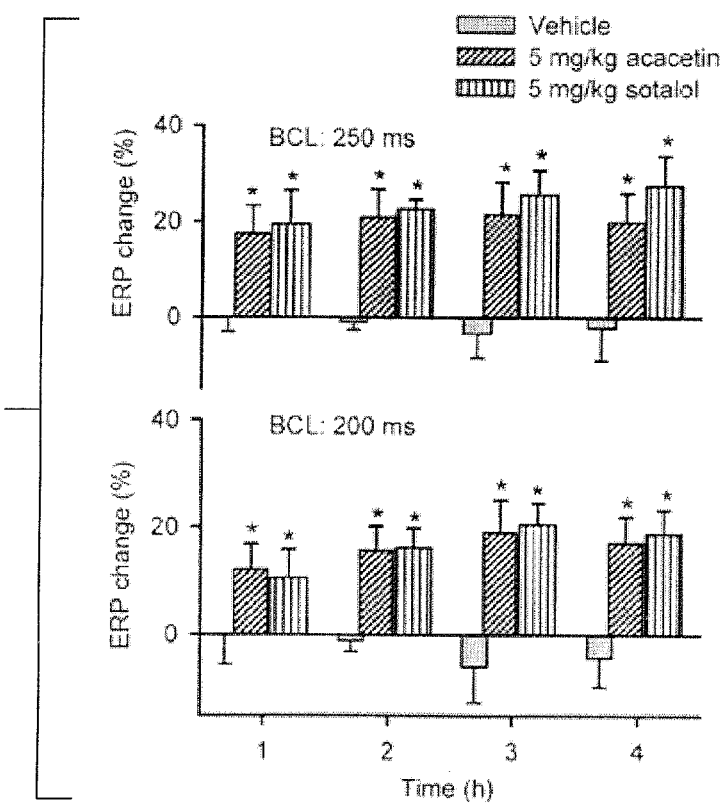
FIG. 11A
FIG. 11B
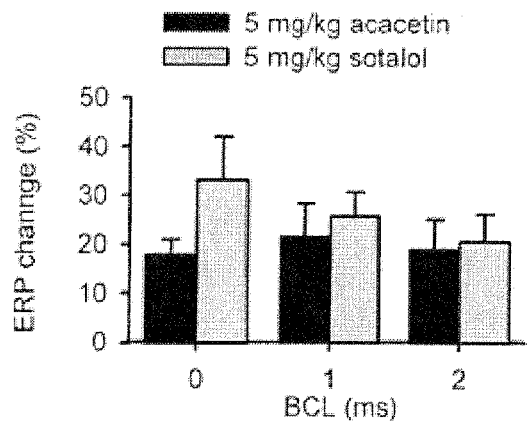
FIG. 11C
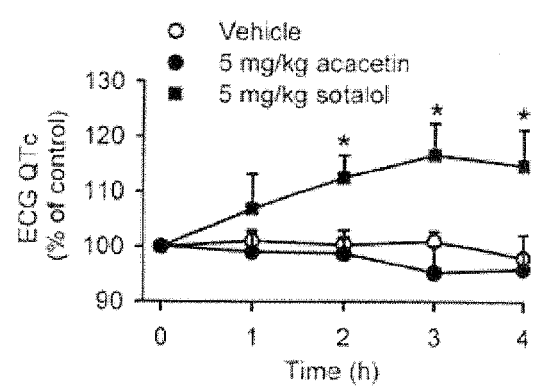

USE OF ACACETIN AND RELATED COMPOUNDS AS POTASSIUM CHANNEL INHIBITORS

CROSS-REFERENCE TO A RELATED APPLICATION

This application claims the benefit of U.S. provisional application Ser. No. 60/892,556, filed Mar. 2, 2007, in its entirety.

FIELD OF THE INVENTION

The present invention is directed to the use of the flavone compound acacetin, and its derivatives and analogues, as potassium channel inhibitors and as anti-atrial fibrillation agents.

BACKGROUND OF THE INVENTION

Atrial fibrillation (AF) is the most common form of cardiac dysrhythmia. The occurrence of AF increases with age: the prevalence rises from 0.5% of people in their 50s, to 5% of people over the age of 65 years, and to nearly 10% of the population over 80 (Benjamin et al., 1998; Wang et al., 2003). AF is a major cause of morbidity and mortality as it increases the risk of death, congestive heart failure, and embolic phenomena including stroke (Benjamin et al., 1998; Wang et al., 2003). AF is believed to be a lifetime risk in an aging population, and therefore is emerging as a major public-health concern (Lloyd-Jones et al., 2004; Lip and Tse, 2007).

Antiarrhythmic drug therapy remains the principal approach for suppressing AF and its recurrence. Class III anti-arrhythmic agents are effective in treating AF (Nademanee, 1992; Roden, 1993), but have major limitations, such as inducing severe ventricular arrhythmia (i.e. long QT syndrome) (Roden and Anderson, 2006). Therefore, a key objective among the current strategies for suppressing AF is the development of antiarrhythmiic agents that preferentially affect atrial rather than ventricular electrical parameters (Burashnikov et al., 2007; Blaauw et al., 2004).

Class III antiarrhythmic agents are drugs that selectively prolong cardiac action potential duration without significant cardiac suppression. Currently available drugs such as sotalol and amiodarone have Class III properties (Sharma et al., 1999; Nattel and Singh, 1999), but they also have other effects. Sotalol also possesses Class II effects (β-adrenoceptor block) causing cardiac depression and is contraindicated in certain susceptible patients (D'Aloia et al., 2005; DeWitt and Waksman, 2004). Amiodarone possesses multiple electrophysiological actions and is limited by side effects (Nademanee, 1992).

Other class III antiarrhythmic agents include dofetilide (UK-68,798), almokalant (H234/09), and E-4031. These compounds, including sotalol, show a predominant block of $I_{Kr}$. However, amiodarone is a blocker of $I_{Ks}$ (Balser et al., 1991), and it also blocks $I_{Na}$, and $I_{Ca}$.

Because $I_{Kr}$ is present in both the atrium and ventricle of the human heart (Wang et al., 1994; Li et al., 1996b), $I_{Kr}$ blockers increase action potential duration and refractoriness in both atria and ventricle. Theoretically they represent potentially useful agents for the treatment of arrhythmias like AF; however, these agents have a liability in that they have an enhanced risk of proarrhythmia at low heart rates. For example, torsades de points has been observed when these compounds are utilized (Roden and Anderson, 2006). This exaggerated effect at low heart rates has been termed "reverse frequency-dependence", and differs from frequency-independent or frequency-dependent actions (Hondeghem, 1992).

In intact human atrial myocytes, an ultra-rapidly activating delayed rectifier K⁺ current $I_{Kur}$, which is also known as the sustained outward K⁺ current ($I_{Ksus}$ or $I_{so}$) has been identified (Wang et al., 1993). This current has properties and kinetics similar to those of the cloned human cardiac K⁺ channel hKv1.5 stably expressed in HEK 293 cells (Fedida et al., 1993). The ultra-rapidly activating delayed rectifier $I_{Kur}$ is found to be functionally present in the atrium, but not in the ventricle of human heart (Li et al, 1996b). Because $I_{Kur}$ is rapidly activated, and has a limited slow inactivation, $I_{Kur}$ is believed to contribute significantly to the repolarization in human atrium. Blockage of $I_{Kur}$ will slow repolarization and prolong refractoriness selectively in the human atrium without causing the delay in ventricular repolarization. A selective $I_{Kur}$ blocker would not produce arrhythmogenic after depolarizations and acquired long QT syndrome observed during treatment with current Class III drugs. Therefore, human atrial $I_{Kur}$ and/or human Kv1.5 are believed to be potential targets for developing selective anti-atrial fibrillation agents (Brendel and Peukert, 2003; Peukert et al., 2003). However, there is no such drug commercially available yet.

BRIEF SUMMARY

The subject invention provides flavone compounds and their use as inhibitors of potassium channel function. In one embodiment, the subject invention provides compounds that inhibit human atrial $T_{Kur}$ and $I_{to}$ that serve as targets for the treatment of atrial arrhythmias.

In a specific embodiment, the subject invention pertains to the use of acacetin, and related compounds, for the treatment of atrial fibrillation (AF).

Acacetin has advantageous properties that make it particularly useful as a preferential $I_{Kur}$ channel blocker. The compounds of the subject invention can be used for the treatment of diseases in mammals, including humans, and especially for the management of human AF.

BRIEF DESCRIPTION OF THE DRAWINGS

FIG. 2A. Time-dependent effects of acacetin on $I_{Kur}$, and the inhibitory effect recovered (by 97%) on washout. FIG. 2B. Voltage-dependent $I_{Kur}$ suppressed by the application of 3, 10 and 30 μM acacetin. FIG. 2C. Concentration-response relationship of $I_{Kur}$ inhibition by acacetin at +40 mV (n=8-20 experiments).

FIG. 3A. Time-dependent effect of acacetin on $I_{to}$ in a representative cell. Acacetin at 3 μM reversibly decreased both $I_{to}$ and $I_{Kur}$. FIG. 3B. Voltage-dependent $I_{to}$ was recorded with the protocol shown in the inset. $I_{Kur}$ was inhibited by 10 μM verapamil to block $I_{Kur}$, and the remaining $I_{to}$ was reduced by 3 and 10 μM acacetin. FIG. 3C. Concentration-response relationship of $I_{to}$ inhibition by acacetin at +40 mV (n=7-16 experiments).

FIG. 4A. Voltage-dependence of steady-sate activation and inactivation was not affected by 10 μM acacetin. FIG. 4B. Recovery of $I_{to}$ from inactivation was slowed by acacetin.

FIG. 5A. Action potentials recorded at 2 Hz with 5 and 10 μM acacetin in a representative cell (left panel), and with 50 μM 4-AP in another cell (right panel). FIG. 5B. Mean values of action potential duration at 50%, 75% and 90% repolarization ($APD_{50}$, $APD_{75}$, and $APD_{90}$). n=6 *P<0.05; P<0.01 vs control. FIG. 5C. Acacetin (10 μM) induced a slight rate-dependent prolongation of APD (n=7, P=NS, 0.5 Hz vs 2 Hz)

FIG. 6A. Membrane currents were recorded in a guinea pig atrial cell using a 2-s ramp from −120 to +50 mV. Carbachol at 5 μM significantly augmented the membrane conductance. Acacetin at 3 μM decreased the increased conductance. FIG. 6B. Membrane currents were recorded with a 300-ms voltage step protocol. FIG. 6C. I-V relationships of carbachol-evoked $I_{K.ACh}$ in the absence and presence of acacetin. Acacetin at 3 and 10 μM substantially blocked $I_{K.ACh}$ (n=5, P<0.01 at −100 to −80 mV, −50 to +60 mV).

FIG. 7A. $I_{Na}$ traces recorded in a representative cell. FIG. 7B. I-V relationships of $I_{Na}$ in the absence and presence of 30 and 100 μM acacetin (n=5-6). FIG. 7C. $I_{Ca.L}$ traces recorded in a cardiac cell. FIG. 7D. I-V relationships of $I_{Ca.L}$ in the absence and presence of 30 and 100 μM acacetin (n=5-7). FIG. 7E. $I_{K1}$ traces recorded in a representative cell with the voltage protocol shown in the inset. FIG. 7F. I-V relationships of $I_{K1}$ in the absence and presence of 30 and 100 μM acacetin (n=6).

FIG. 8A. Voltage-dependent $I_{hERG}$ was reversibly inhibited by 30 μM acacetin. FIG. 8B. Concentration-response relationship of $I_{hERG.tail}$ block by acacetin (+40 mV, n=8-14 experiments). FIG. 8C. Voltage-dependent $I_{Ks}$ was inhibited by 30 μM acacetin in a HEK 293 cell stably expressing the hKCNQ1/hKCNE1 genes. FIG. 8D. Concentration-response relationship of $I_{Ks.step}$ inhibition by acacetin at +40 mV (n=7-12 experiments).

FIG. 9A. Acacetin at 30 μM did not affect ECG parameters. FIG. 9B. Quinidine at 10 μM slowed heart rate, and prolonged QTc interval of ECG. FIG. 9C. Mean values of heart rate before and after 30 μM acacetin or 10 μM quinidine (P<0.01 vs before treatment). FIG. 9D. Mean values of QTc interval of ECG before and after 30 μM acacetin or 10 μM quinidine (P<0.01 vs before treatment).

FIG. 10A. ERP measurement by S1 and S2 stimuli. FIG. 10B. Sustained AF was triggered by the S2 when right atrial ERP was measured at 200 ms BCL. FIG. 10C. The AF was no longer triggered 2 h post-treatment with 5 mg/kg acacetin.

FIGS. 11A, 11B, and 11C show the effects of acacetin and sotalol on left atrial ERP and QTc in anesthetized dogs. FIG. 11A. Percent changes in left atrial ERP at BCLs of 250 and 200 ms relative to the basal level (before intraduodenal administration, *P<0.05 vs vehicle, ANOVA). FIG. 11B. Sotalol, but not acacetin, showed 'reverse-rate dependent' prolongation of ERP (data from three hours post administration). FIG. 11C. Sotalol, but not acacetin, prolonged the QTc interval in anesthetized dogs (P<0.05).

FIG. 12A. Typical recordings show ECG (lead II) and MAP traces recorded using MAP recording and pacing catheters introduced into right atrium and left ventricle, respectively. FIG. 12B. AF was generated using S1-S2 stimuli (arrow) at 100 ms BCL with continuous bilateral vagal stimulation and ventricular pacing. ECG follows ventricular pacing rhythm.

FIG. 13A. Acacetin at 2.5, 5, and 10 mg/kg, but not vehicle, reduced the incidence of AF 1.5-2.5 h after intraduodenal administration. Sotalol also reduced the incidence of AF in anesthetized dogs. FIG. 13B. Acacetin at 5 and 10 mg/kg significantly prevented AF (*P<0.05 vs vehicle, Fisher exact test).

DETAILED DESCRIPTION OF THE INVENTION

The subject invention provides flavone compounds and their use as inhibitors of potassium channel function. In one embodiment, the subject invention provides compounds that inhibit human atrial $T_{Kur}$ and $I_{to}$ that serve as targets for the treatment of atrial arrhythmias.

In an embodiment specifically exemplified herein, a flavone compound is used to treat atrial fibrillation. In a preferred embodiment, acacetin is used to treat atrial fibrillation in humans.

In accordance with the subject invention, it has been found that the natural flavone acacetin is a novel, orally-effective, atrial-selective, anti-arrhythmic agent for the treatment of AF. Advantageously, it has been found that acacetin preferentially inhibits $I_{Kur}$ and $I_{to}$ prolongs APD in human atrial myocytes, prolongs ERP, and prevents AF induction in anesthetized dogs. In addition to the blockade of atrial $I_{Kur}$, $I_{to}$ and $I_{KACh}$, the anti-peroxidative and anti-inflammatory effects of acacetin are also be of benefit.

Figure 1A:
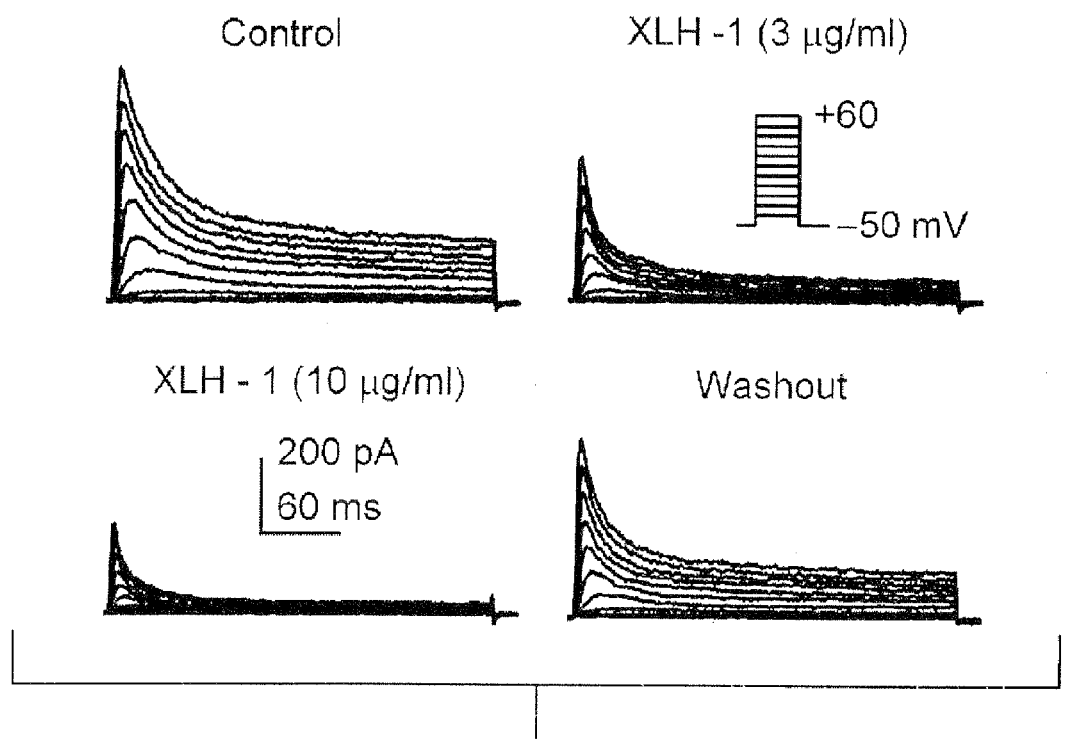
FIGS. 1A and 1B show the effects of XLH-I on transient outward potassium current ($I_{to}$, FIG. 1A) and sustained potassium current ($I_{Kur}$, FIG. 1B) in representative human atrial myocytes.
Figure 1B:
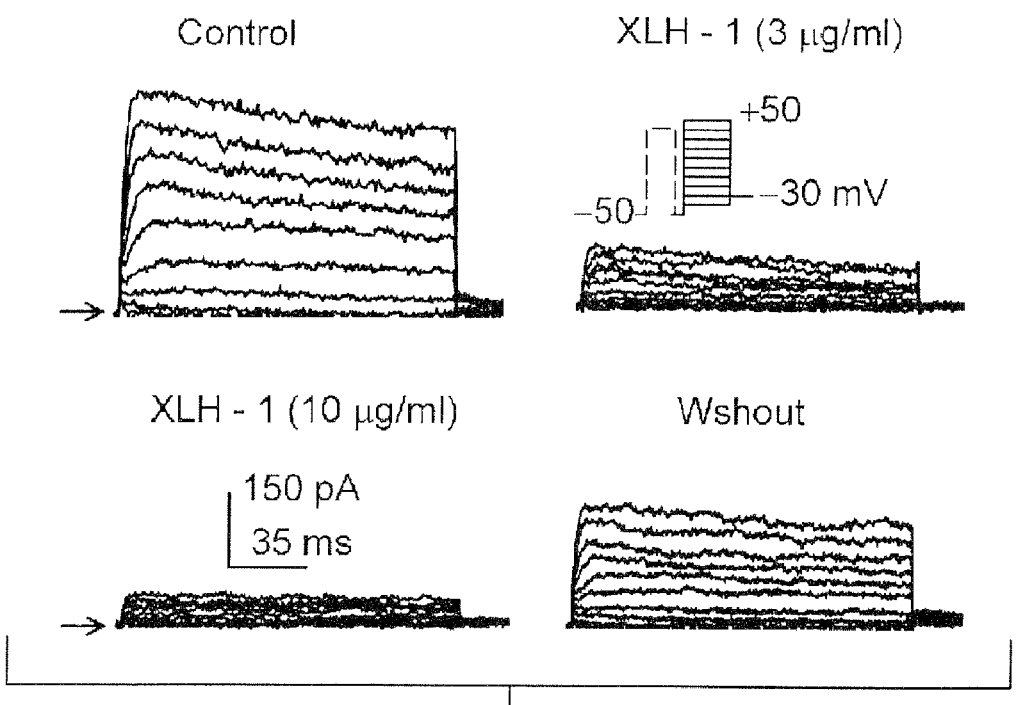

The effects of ethanol extracts from the Snow-Lotus-Flowers namely "Xue-Lian-Hua" in Chinese (the whole herb of *Saussurea laniceps*) on cardiac membrane currents in human atrial myocytes were studied. The chloroform fraction extract (XLH-I) of the ethanol extracts showed a substantial inhibition of $I_{Kur}$ and $I_{to}$ in human atrial myocytes (FIG. 1). Then, several compounds (Compounds A, B, C, and D) were isolated from the XLH-I extract. After a series of tests in human atrial myocytes, compound A was found to have a blocking effect on $I_{Kur}$ and $I_{to}$ in human atrial myocytes. The chemical structure of compound A was then determined to be acacetin.

Acacetin is a flavone compound (5,7-dihydroxy-4'-methoxyflavone) that is broadly distributed in plant pigments, universally present in vascular plants and responsible for much of the colors in nature (Cody, 1988). Acacetin has been reported to possess anti-peroxidative, anti-inflammatory, and antiplasmodial effects (Liao et al., 1999; Kraft et al., 2003), to enhance differentiation-inducing activity in HL-60 cells (Kawaii et al., 2000), and to exert an anti-cancer action in several types of cancers, including human prostate cancer, lung cancer, and HepG2 (Singh et al., 2005; Pan et al., 2006; Hsu et al., 2004). In addition, acacetin can also inhibit glutathione reductase, cytochrome P450 and topoisomerase I-catalyzed DNA religation (Zhang et al., 1997; Doostdar et al., 2000).

In addition to acacetin, the subject invention further contemplates the use of derivatives, analogs, salts, glycosides, esters, amide and/or stereoisomers thereof.

In accordance with the present invention, acacetin inhibits $I_{Kur}$ and $I_{to}$, prolongs action potential duration in human atrial myocytes, and blocks $I_{K.ACh}$ in guinea pig atrial cells. This compound has no effect on $I_{Na}$, $I_{Ca,L}$, and $I_{K1}$ in guinea pig ventricular myocytes, and shows a weak inhibition of hERG channels and $I_{Ks}$ channels stably expressed in HEK 293 cells. Importantly, acacetin dose not increase QTc interval of EGC in anesthetized dogs and isolated rabbit hearts.

It is generally accepted that cardiac repolarization and refractoriness are determined by the balance of inward $Ca^{2+}$ and outward $K^+$ currents. $I_{Kur}$ and $I_{to}$ are major outward currents in the human atrium, and therefore play important roles in human atrial repolarization (Courtemanche et al., 1999). Previous work has demonstrated that $I_{Kur}$ is functionally present in the atrium, but not in the ventricle of the human heart (Li et al., 1996b). Therefore, $I_{Kur}$ is an attractive target for selective anti-AF agents (Nattel et al., 2002).

In accordance with the subject invention, it has been found that acacetin inhibits human atrial $I_{Kur}$ in a concentration-dependent manner with an $IC_{50}$ of 3.2 μM (FIG. 2). This concentration is lower than those observed previously in anti-peroxidative, anti-inflammatory and anti-mutagenic studies (Pan et al., 2006; Cholbi et al., 1991; Kraft et al., 2003). In addition, acacetin blocked $I_{to}$ with an $IC_{50}$ of 9.2 μM (FIG. 3), and slowed the recovery of $I_{to}$ from inactivation without affecting the voltage-dependence of the current (FIG. 4). The inhibition of $I_{to}$ by acacetin can also contribute to the prolongation of APD in human atrium. Acacetin at 5 and 10 μM significantly prolonged APD at 50%, 75% and 90% repolarization at 0.5, 1.0, and 2.0 Hz (FIG. 5). The prolongation of APD increases effective refractory period and terminates AF.

Vagal stimulation shortens the atrial APD and effective refractory period, and therefore vagal nerve tone plays a crucial role in AF (Schauerte et al., 2000; Zipes et al., 1974). The acetylcholine-activated potassium current $I_{K,ACh}$ mediates much of the cardiac response to vagal nerve stimulation via muscarinic M-receptors activation (Hashimoto et al., 2006; Liu and Nattel, 1997). $I_{K,ACh}$ and/or M-receptor expression are up-regulated in AF patients (Bosch et al., 1999) and in AF induced by experimental heart failure in the dog (Shi et al., 2004). Therefore, the blockage of $I_{K,ACh}$ should terminate AF induced by the increased vagal nerve tone. The selective $I_{K,ACh}$ blocker tertiapin, a bee venom peptide, terminated AF caused by stimulating vagal nerve in dogs (Hashimoto et al., 2006).

Figure 6A:
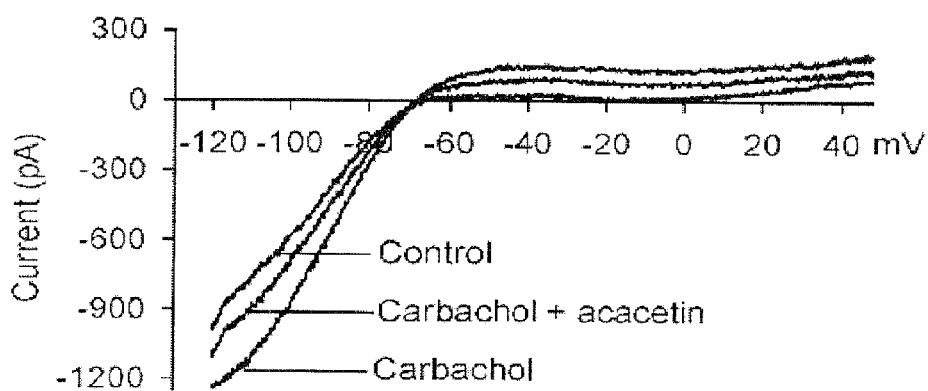
FIGS. 6A, 6B, and 6C show the inhibition of $I_{K.ACh}$ by acacetin in guinea pig atrial myocytes.
Figure 6B:
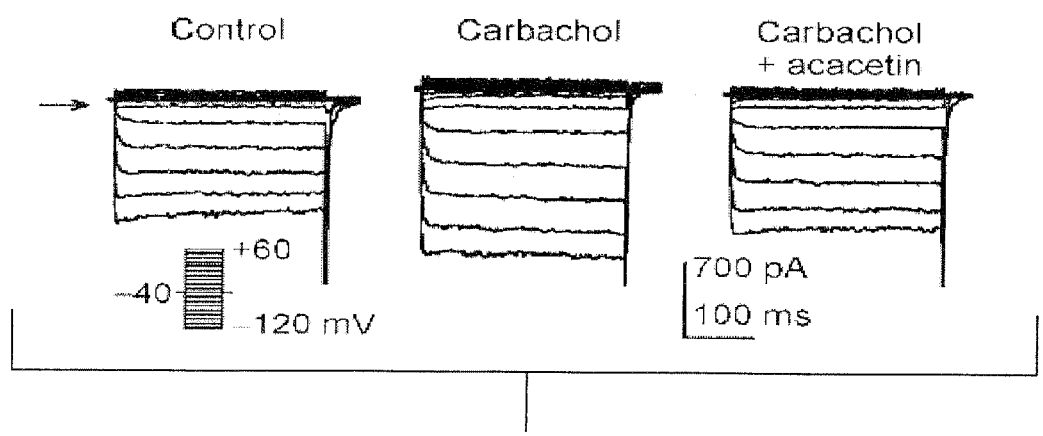

In accordance with the subject invention, it has been found that acacetin at 3 and 10 μM substantially inhibits carbachol-elicited $I_{K,ACh}$ in guinea pig atrial myocytes (FIG. 6), indicating that acacetin is effective in terminating AF induced by $I_{K,ACh}$ activation.

Acacetin at 30-100 μM showed no inhibition of cardiac $I_{Na}$, $I_{Ca,L}$, and $I_{K1}$ in guinea pig ventricular myocytes (FIG. 7). These results suggest that acacetin should not reduce cardiac conduction velocity or contractility, and should not depolarize cell membrane as observed in class I and class IV antiarrhythmic drugs.

On the other hand, acacetin inhibited $I_{hERG}$ with an $IC_{50}$ of 32.4 μM in HEK 293 cell line, and also suppressed human cardiac $I_{Ks}$ with an $IC_{50}$ of 81.4 μM in HEK 293 cells stably expressing hKCNQ1/hKCNE1 channels (FIG. 8). However, acacetin (30 μM), in contrast to quinidine (10 μM), did not affect heart rate, and did not cause a QTc prolongation in isolated hypokalemic rabbit hearts (FIG. 9).

Blockade of the ultra-rapid delayed rectifier current $I_{Kur}$ (or Kv1.5) channel has been proposed as a novel target for the development of safer and potentially more effective atrial antiarrhythmic agents (Pecini et al., 2005). There are four structurally distinct synthesized antiarrhythmic agents that have been described as possessing $I_{Kur}$ block as part of their spectra of actions: NIP-141 (Seki et al., 2002), AVE0118 (de Haan et al., 2006; Gogelein et al., 2004), RSD1235 (Fedida et al., 2005), and DPO-1 (Regan et al., 2006).

As discussed above, it has been determined that acacetin, a $I_{Kur}$ blocker, also blocks $I_{to}$ and $I_{K,ACh}$. These properties are favorable for terminating AF.

Acacetin (5 mg/kg) significantly prolonged atrial ERP without prolonging QTc interval in anesthetized dogs after intraduodenal administration (FIGS. 10 & 11, Tables 1 & 2), which differs from sotalol, in that it prolonged both atrial ERP and QTc. These results suggest that acacetin has an anti-AF potential effect with no proarrhythmic potential. Indeed, the anti-AF effect was proven in anesthetized dogs, since acacetin at 5 and 10 mg/kg significantly prevented AF induction (FIG. 13).

In addition, no animal death is found in mice with a maximal oral administration of acacetin (900 mg/kg) during a two-week observation period, indicating that acacetin has low or no acute toxicity.

Finally, a comparative study (Table 3) shows that the derivatives/analogs studied have less ion channel selectivity for Kv1.5 and hERG channels (A-2) or have less effect (A-4, A-5, A-6, A-2-11, A-2-12, A-2-13, A-2-14) or no effects (A-9, A-10, A-11, A-12) on Kv1.5.

TABLE 1 shows the effects of acacetin and sotalol on the right atrial ERP in anesthetized dogs.

| BCL | ERP (ms) | | |
|---|---|---|---|
| | 300 | 250 | 200 ms |
| Acacetin 5 mg/kg (n = 5) | | | |
| Pre-treatment | 100.8 ± 7.9 | 96.5 ± 6.9 | 87.2 ± 7.9 |
| 1 | 108.5 ± 3.7 | 98.8 ± 3.6 | 89.5 ± 2.7 |
| 2 | 118.5 ± 5.3* | 118.5 ± 11.6* | 104.5 ± 8.9* |
| 3 | 124.1 ± 9.7* | 112.3 ± 6.3* | 106.5 ± 7.9* |
| 4 post-treatment | 125.2 ± 11.2* | 116.4 ± 11.2* | 105.1 ± 7.5* |
| Sotalol 5 mg/kg (n = 5) | | | |
| Pre-treatment | 100.3 ± 9.4 | 96.3 ± 8.3 | 88.7 ± 3.9 |
| 1 | 128.1 ± 8.6* | 122.5 ± 6.6* | 99.4 ± 3.2 |
| 2 | 143.1 ± 12.2* | 128.6 ± 8.9* | 105.1 ± 5.1* |
| 3 | 138.5 ± 8.7* | 128.2 ± 7.6* | 111.3 ± 9.3* |
| 4 post-treatment | 139.4 ± 8.3* | 126.3 ± 6.9* | 112.8 ± 9.1* |
| Vehicle (n = 4) | | | |
| Pre-treatment | 108.1 ± 6.2 | 99.1 ± 6.4 | 93.1 ± 6.1 |
| 1 | 111.9 ± 6.5 | 106.3 ± 5.9 | 98.1 ± 7.1 |
| 2 | 108.8 ± 7.3 | 100.1 ± 9.2 | 93.2 ± 8.2 |
| 3 | 108.2 ± 9.0 | 98.1 ± 10.4 | 91.8 ± 9.2 |
| 4 post-treatment | 100.5 ± 8.9 | 96.9 ± 9.8 | 91.3 ± 8.7 |

*P < 0.05 vs pre-treatment

TABLE 2 shows the effects of acacetin and sotalol on the left atrial ERP in anesthetized dogs.

| BCL | ERP (ms) | | |
|---|---|---|---|
| | 300 | 250 | 200 ms |
| Acacetin 5 mg/kg (n = 5) | | | |
| Pre-treatment | 105.1 ± 3.9 | 89.9 ± 3.5 | 94.4 ± 3.4 |
| 1 | 122.1 ± 9.4* | 116.5 ± 8.3* | 106.5 ± 7.2* |
| 2 | 125.1 ± 7.8* | 119.8 ± 8.0* | 110.1 ± 6.8* |
| 3 | 126.7 ± 8.6* | 122.5 ± 8.9* | 113.5 ± 7.9* |
| 4 post-treatment | 125.1 ± 7.8* | 118.9 ± 7.5* | 111.5 ± 6.5* |

TABLE 2-continued shows the effects of acacetin and sotalol on the left atrial ERP in anesthetized dogs.

| BCL | ERP (ms) | | |
|---|---|---|---|
| | 300 | 250 | 200 ms |

| Sotalol 5 mg/kg (n = 5) | | | |
|---|---|---|---|
| Pre-treatment | 99.4 ± 3.7 | 94.3 ± 3.1 | 88.8 ± 3.7 |
| 1 | 115.6 ± 5.7 | 113.8 ± 9.2* | 99.4 ± 3.2* |
| 2 | 125.6 ± 8.5* | 116.9 ± 3.2* | 105.1 ± 5.1* |
| 3. | 132.5 ± 12.4* | 120.1 ± 2.6* | 109.3 ± 7.5* |
| 4 post-treatment | 135.6 ± 6.9* | 121.9 ± 6.7* | 107.6 ± 4.2* |

| Vehicle control (n = 4) | | | |
|---|---|---|---|
| Pre-treatment | 107.8 ± 7.4 | 100.1 ± 7.7 | 94.5 ± 7.1 |
| 1 | 107.5 ± 8.2 | 104.3 ± 8.1 | 97.5 ± 6.9 |
| 2 | 103.8 ± 6.3 | 101.9 ± 6.5 | 97.3 ± 5.9 |
| 3 | 99.9 ± 6.7 | 92.5 ± 5.3 | 88.2 ± 5.8 |
| 4 | 100.1 ± 7.1 | 92.5 ± 4.1 | 86.3 ± 6.8 |

*$P < 0.05$ vs pre-treatment

TABLE 3 shows the comparative observation of acacetin with its derivatives/analogs for the effects of blocking Kv1.5 and hERG channels

| Compounds/derivatives | Kv1.5 (IC$_{50}$, μM) | hERG (IC$_{50}$, μM) |
|---|---|---|
| Acacetin | 3.4 | 32.4 |
| A-2 | 2.04 | 4.1 |
| A-4 | 9.0 | 21.9 |
| A-5 | 23.5 | 13.0 |
| A-6 | 13.7 | 57.9 |
| A-9 | NE | NE |
| A-10 | NE | NT |
| A-11 | NE | NE |
| A-12 | NE | NE |
| A-2-11 | WE | NT |
| A-2-12 | WE | NT |
| A-2-13 | WE | NT |
| A-2-14 | WE | NT |

Note:
NE, no effect;
NT, not tested;
WE, weak effect (<50% inhibition at 100 μM)

Acacetin, and Its Derivatives and Analogues

Structure of Acacetin

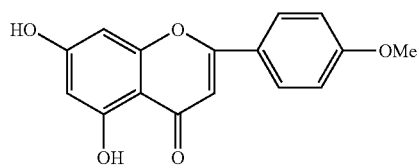

Derivatives from Synthesis

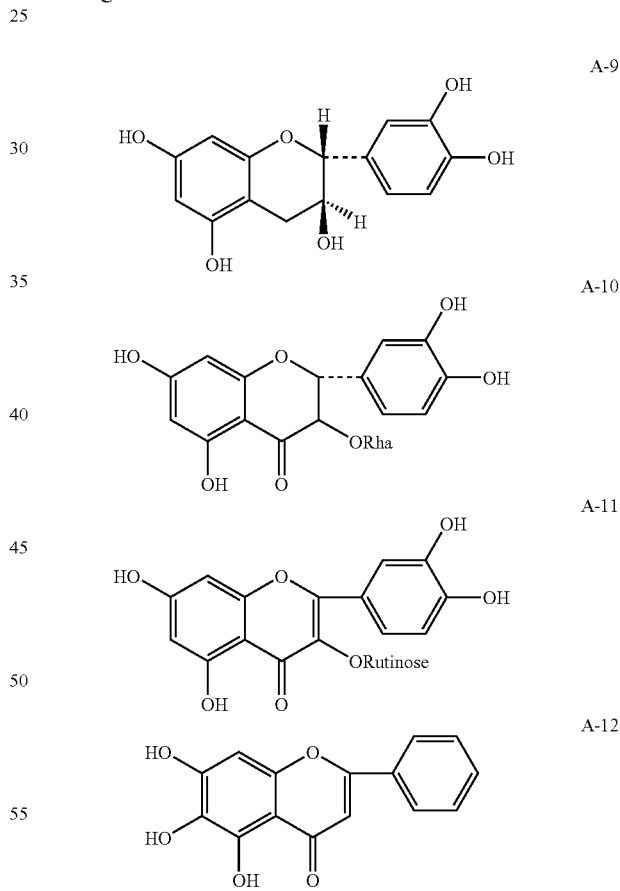

| | R$_1$ | R$_2$ | R$_3$ |
|---|---|---|---|
| A | OH | H | OH |
| A-02-11-11 | CH$_3$COO | H | OH |
| A-02-11-12 | benzoate | H | OH |
| A-02-11-13 | CH$_3$O | H | OH |
| A-02-11-14 | CH$_3$CH$_2$O | H | OH |
| A-2 | OH | H | p-methoxybenzoate |
| A-3 | p-methoxybenzoate | H | OH |
| A-4 | H | H | H |
| A-5 | H | Cl | H |
| A-6 | H | CH$_3$ | H |

Analogues from Natural Resources

Physical Data of Acacetin and Its Derivatives

Acacetin

Acacetin: a pale yellow powder; $C_{16}H_{12}O_5$; MW. 284; mp 263° C.; $^1$H-NMR (400 MHz, DMSO): 6.82 (s, H-3), 6.47 (d, J=1.9 Hz, H-8), 6.18 (d, J=1.9 Hz, H-6), 7.98 (d, J=8.8 Hz, H-2', 6'), 7.07 (d, J=8.8 Hz, H-3', 5'), 3.85 (s, 4'-OCH$_3$).

Derivatives from Synthesis

A-02-11-11: a pale yellow powder; $C_{18}H_{14}O_6$; MW. 326; mp 279° C.; $^1$H-NMR (400 MHz, DMSO): 6.82 (s, H-3), 6.45 (d, J=1.9 Hz, H-8), 6.12 (d, J=1.9 Hz, H-6), 7.98 (d, J=8.8 Hz, H-2', 6'), 7.07 (d, J=8.8 Hz, H-3', 5'), 3.85 (s, 4'-OCH$_3$), 2.01 (s).

A-02-11-12: a pale yellow powder; $C_{23}H_{16}O_6$; MW. 388; mp 282° C.; $^1$H-NMR (400 MHz, DMSO): 6.81 (s, H-3), 6.43 (d, J=1.9 Hz, H-8), 6.16 (d, J=1.9 Hz, H-6), 7.97 (d, J=8.8 Hz, H-2', 6'), 7.02 (d, J=8.8 Hz, H-3', 5'), 3.85 (s, 4'-OCH$_3$), 7.20-7.42 (m).

A-02-11-13: a pale yellow powder; $C_{17}H_{14}O_5$; MW. 298; mp 174° C.; $^1$H-NMR (400 MHz, DMSO): 6.80 (s, H-3), 6.46 (d, J=1.9 Hz, H-8), 6.16 (d, J=1.9 Hz, H-6), 7.97 (d, J=8.8 Hz, H-2', 6'), 7.02 (d, J=8.8 Hz, H-3', 5'), 3.86 (s, 4'-OCH$_3$), 3.84 (s, 7-OCH$_3$).

A-02-11-14: a pale yellow powder; $C_{18}H_{16}O_5$; MW. 312; mp 165° C.; $^1$H-NMR (400 MHz, DMSO): 6.80 (s, H-3), 6.45 (d, J=1.9 Hz, H-8), 6.17 (d, J=1.9 Hz, H-6), 7.96 (d, J=8.8 Hz, H-2', 6'), 7.01 (d, J=8.8 Hz, H-3', 5'), 3.83 (s, 4'-OCH$_3$), 3.89 (dd, J=5.0 Hz), 1.33 (t, J=5.1 Hz).

A-2: a pale yellow powder; $C_{24}H_{18}O_7$; MW. 418; mp 275° C.; $^1$H-NMR (400 MHz, DMSO): 6.80 (s, H-3), 6.42 (d, J=1.9 Hz, H-8), 6.13 (d, J=1.9 Hz, H-6), 7.93 (d, J=8.8 Hz, H-2', 6'), 7.01 (d, J=8.8 Hz, H-3', 5'), 3.85 (s, 4'-OCH$_3$), 7.79 (d, J=8.2 Hz, 2H), 6.92 (d, J=8.2 Hz, 2H), 3.74 (s, —OCH$_3$).

A-3: a pale yellow powder; $C_{24}H_{18}O_7$; MW. 418; mp 265° C.; $^1$H-NMR (400 MHz, DMSO): 6.85 (s, H-3), 6.32 (d, J=1.9 Hz, H-8), 6.21 (d, J=1.9 Hz, H-6), 7.92 (d, J=8.8 Hz, H-2', 6'), 7.03 (d, J=8.8 Hz, H-3', 5'), 3.85 (s, 4'-OCH$_3$), 7.75 (d, J=8.2 Hz, 2H), 6.99 (d, J=8.2 Hz, 2H), 3.82 (s, —OCH$_3$).

A-4: a yellow powder; $C_{16}H_{12}O_3$; MW. 252; mp 164° C.; $^1$H-NMR (400 MHz, DMSO): 6.71 (s, H-3), 6.92-7.64 (m, H-5, 6, 7, 8), 7.86 (d, J=8.8 Hz, H-2', 6'), 6.82 (d, J=8.8 Hz, H-3', 5'), 3.73 (s, 4'-OCH$_3$).

A-5: a yellow powder; $C_{16}H_{11}ClO_3$; MW. 286; mp 194° C.; $^1$H-NMR (400 MHz, DMSO): 6.67 (s, H-3), 7.34 (d, J=1.2 Hz, H-5), 7.12 (m, H-7), 6.89 (m, H-8), 7.56 (d, J=8.8 Hz, H-2', 6'), 6.82 (d, J=8.8 Hz, H-3', 5'), 3.75 (s, 4'-OCH$_3$).

A-6: a yellow powder; $C_{17}H_{14}O_3$; MW. 266; mp 179° C.; $^1$H-NMR (400 MHz, DMSO): 6.73 (s, H-3), 7.21 (d, J=1.2 Hz, H-5), 7.02 (m, H-7), 6.72 (m, H-8), 7.83 (d, J=8.8 Hz, H-2', 6'), 6.80 (d, J=8.8 Hz, H-3', 5'), 3.71 (s, 4'-OCH$_3$), 2.35 (s, 6-CH$_3$).

Analogues from Natural Resources

A-9: a white amorphous powder; $C_{15}H_{14}O_6$; mp 246-247° C.; $[\alpha]^{20}_D$ 52.3°(c 0.128, in MeOH); LC-MS: 290 [M]$^+$; $^1$H-NMR (400 MHz, CD$_3$OD): 6.92 (1H, d, J=2.0 Hz, 2'-H), 6.69 (1H, d, J=8.0 Hz, 5'-H), 6.74 (1H, dd, J=8.0, 2.0 Hz, 6'-H), 5.88 (1H, d, J=2.0 Hz, 8-H), 5.86 (1H, d, J=2.0 Hz, 6-H), 4.76 (1H, s, 2-H), 4.11 (1H, m, 3-H), 2.80 (1H, dd, J=17.0, 4.5 Hz, 4-H), 2.68 (1H, dd, J=17.0, 3.0 Hz, 4-H).

A-10: white needles; $C_{21}H_{22}O_{11}$; LC-MS: 466 [M]$^+$; m.p. 166-168° C.; $[\alpha]^{25}_d$: +110.5°(0.15, MeOH); $^1$H-NMR (DMSO, 400 MHz): 12.60 (1H, s, 5-OH), 10.5 (1H, s, 7-OH), 7.13 (1H, Ar—H), 6.85 (2H, m, Ar—H), 5.93 (2H, s, 6, 8-H), 5.30 (1H, d, J=10 Hz, 2-H), 4.97 (1H, d, J=10 Hz, 3-H), 4.70 (1H, d, J=7 Hz, 1"-H).

A-11: a yellow powder; $C_{24}H_{16}O_9$; mp 190-192° C.; LC-MS: 610 [M]$^+$, $^1$H-NMR (CD$_3$OD, 400 MHz): 6.13 (1H, d, J=1.8 Hz, H-6), 6.32 (1H, d, J=1.8 Hz, H-8), 7.61 (1H, d, J=2.1 Hz, H-2), 6.81 (1H, d, 8.4 Hz, H-5'), 7.57 (1H, dd, J=2.1, 8.4 Hz, H-6'), 5.05 (1H, d, J=7.2 Hz, H-1"); 4.47 (1H, s, H-2'''), 1.07 (3H, d, J=6 Hz, CH$_3$-6''').

A-12: a yellow powder; $C_{15}H_{10}O_5$; mp 273-275° C.; LC-MS: 270 [M]$^+$; $^1$H-NMR (CD$_3$OD, 400 MHz): 12.70 (1H, S, C$_5$—OH), 10.60 (1H, S, C$_7$—OH), 8.48 (1H, s, C$_6$—OH), 8.04 (2H, m, C$_{2',6'}$—H), 7.57 (3H, m, C$_{3',4',5'}$-H), 6.91 (1H, s, C$_3$—H), 6.62 (1H, s, C$_8$—H).

Salts

Salts are also within the scope of this invention. Reference to a flavone compound of the subject invention is understood to include reference to salts thereof, unless otherwise indicated. The term "salt(s)", as employed herein, denotes acidic and/or basic salts formed with inorganic and/or organic acids and bases. In addition, when a compound contains both a basic moiety and an acidic moiety, zwitterions ("inner salts") may be formed and are included within the term "salt(s)" as used herein.

Pharmaceutically acceptable (i.e., non-toxic, physiologically acceptable) salts are preferred, although other salts are also useful, e.g., in isolation or purification steps which may be employed during preparation. Salts of the compounds may be formed, for example, by reacting a compound with an amount of acid or base, such as an equivalent amount, in a medium such as one in which the salt precipitates or in an aqueous medium followed by lyophilization.

Salts that are contemplated according to the subject invention include those described in U.S. Patent Application No. 2007/0203157, which is incorporated by reference herein in its entirety.

Stereoisomers

All stereoisomers of the present compounds, such as those which may exist due to asymmetric carbons, including enantiomeric forms (which may exist even in the absence of asymmetric carbons) and diastereomeric forms, are contemplated within the scope of this invention. Individual stereoisomers of the compounds of the invention may, for example, be substantially (i.e. more than 90% and, preferably, more than 95%) free of other isomers, or may be admixed, for example, as racemates or with all other, or other selected, stereoisomers. The chiral centers of the present invention can have the S or R configuration as defined by the IUPAC 1974 Recommendations.

Pharmaceutical Compositions

The present invention also provides pharmaceutical compositions comprising at least one of the flavone compounds or salts thereof capable of preventing or treating one or more of the aforementioned disorders in an amount effective therefor, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

As used herein, unless the context or explicit language dictates otherwise, reference to a "pharmaceutical carrier" or "pharmaceutical vehicle" or other such term, excludes the compounds and materials with which acacetin (and/or the other flavones, analogs, derivatives, etc) are associated in nature. Thus, unless the context or explicit language dictates otherwise, reference to a "pharmaceutical carrier" or "pharmaceutical vehicle" would not include, for example, a plant or natural unaltered plant material associated with flavones in nature. Reference herein to "isolated" acacetin (or other "isolated" compound) refers to acacetin (or other compound) that has been produced synthetically or has been isolated to remove it from some or all of the other compounds with which it exists in nature.

The compounds of the subject invention may be administered by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents.

The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. In the case where the compounds are being administered to prevent or treat arrhythmias, the compounds may be administered to achieve chemical conversion to normal sinus rhythm, or may optionally be used in conjunction with electrical cardioconversion.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The compounds may also be delivered through the oral cavity by sublingual and/or buccal administration. Molded tablets, compressed tablets or freeze-dried tablets are exemplary forms which may be used.

Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non-irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.001 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to the aforementioned disorders.

The compounds of the present invention may be employed alone or in combination with each other and/or other suitable therapeutic agents useful in the treatment of the aforementioned disorders or other disorders, including: other antiarrhythmic agents such as Class I agents (e.g., propafenone), Class II agents (e.g., carvadiol and propranolol), Class III agents (e.g., sotalol, dofetilide, amiodarone, azimilide and ibutilide), Class IV agents (e.g., diltiazem and verapamil), 5HT antagonists (e.g., sulamserod, serraline and tropsetron); calcium channel blockers; cyclooxygenase inhibitors (i.e., COX-1 and/or COX-2 inhibitors) such as aspirin, indomethacin, ibuprofen, piroxicam, Naproxen®, Celebrex®, Vioxx® and NSAIDs; anti-platelet agents; diruetics; and other agents as set forth in U.S. Published Patent Application No. 2007-0203157 A1 which is incorporated herein in its entirety.

The above other therapeutic agents, when employed in combination with the compounds of the present invention, may be used, for example, in those amounts indicated in the Physicians' Desk Reference (PDR) or as otherwise determined by one of ordinary skill in the art.

Materials and Methods 1.1 Human Cardiac Myocyte Preparation

Atrial cells were isolated from specimens of human right atrial appendage obtained from patients (56.1±4.7 years old) undergoing coronary artery bypass grafting. The procedure for obtaining the human tissue was approved by the Ethics Committee of the University of Hong Kong based on the patients' consent. All patients were free from supraventricular tachyarrythmias, and the atria were grossly normal at the time of surgery. After excision, the samples were quickly immersed in oxygenated, normally $Ca^{2+}$-free cardioplegic solution for transport to the laboratory. Atrial myocytes were enzymatically dissociated as described previously (Tian et al., 2006; Gao et al., 2004). Briefly, the atrial tissue was minced, and gently agitated by continuous bubbling with 100% $O_2$ in a $Ca^{2+}$-free Tyrode solution for 15 min (5 min at a time in fresh solutions), and then incubated for 50 min in a similar solution containing 150-200 U/ml collagenase (CLS II, Worthington Biochemical, Freehold, N.J., USA), 0.2 mg/ml protease (type XXIV, Sigma-Aldrich Chemical, St Louis, Mo., USA.) and 1 mg/ml bovine serum albumin (Sigma-Aldrich). After then, the chunks were re-incubated in a fresh enzyme solution of the same composition but no protease. The quantity and quality of isolated cells were monitored under a microscope. When the cell yield appeared optimal, the chunks were suspended in a high K medium containing (mM) 10 KCl, 120 K-glutamate, 10 $KH_2PO_4$, 1.8 $MgSO_4$, 10 taurine, 10 HEPES, 0.5 EGTA, 20 glucose, 10 mannitol, pH was adjusted to 7.3 with KOH and gently blown with a pipette. The isolated myocytes were kept at room temperature in the medium at least 1 h before use.

1.2. Guinea Pig Cardiac Myocyte Preparation

Guinea pigs of either gender (250-300 g) were sacrificed by cervical dislocation after anesthetization with pentobarbital (40 mg kg, i.p.). The procedure related to the use of animals in this invention was approved by the Animal Care and Use Committee for Teaching and Research of University of Hong Kong in accordance with the Guide for the Care and Use of Laboratory Animals (Institute of Laboratory Animal Resources, Commission on Life Sciences, National Research Council, 1996). Left atrial and ventricular myocytes from guinea pig hearts were enzymatically dissociated by the procedure described previously (Li et al., 2002a) and the isolated myocytes were kept in the $K^+$ storage medium.

1.3. Cell Line Culture

The established HEK 293 cell lines stably expressing the hERG channel gene, Kv1.5 (Tang et al., 2007), or recombinant human cardiac KCNQ1/KCNE1 channel current ($I_{Ks}$) (Dong et al., 2006) was maintained separately in Dulbecco's modified eagle medium (Invitrogen) supplemented with 10% fetal bovine serum and containing 400 μg/ml G418 (for hERG or Kv1.5 channels) or 100 μg/ml hygromycin (for $I_{Ks}$).

1.4. Solutions and Drugs

The $Ca^{2+}$-free cardioplegic solution for specimen transport contained (in mM) 50 $KH_2PO_4$, 8 $MgSO_4$, 5 adenosine, 10 HEPES, 140 glucose, 100 mannitol, 10 taurine, pH was adjusted to 7.3 with KOH. Tyrode solution contained (in mM) 140 NaCl, 5.4 KCl, 1 $MgCl_2$, 1 $CaCl_2$, 0.33 $NaH_2PO_4$, 10 HEPES, 10 glucose, pH was adjusted to 7.4 with NaOH. The pipette solution contained (in mM) 20 KCl, 110 K-aspartate, 1 $MgCl_2$, 10 HEPES, 5 EGTA, 0.1 GTP, 5 $Na_2$-phosphocreatine, and 5 $Mg_2$-ATP, pH was adjusted to 7.2 with KOH. For $I_{to}$ and $I_{Kur}$ recording, $BaCl_2$ (200 μM) and $CdCl_2$ (200 μM) were added to the superfusion to block $I_{K1}$ and $I_{Ca,L}$. Atropine (1.0 μM) was used to minimize possible $I_{K.ACh}$ contamination during the current recording. For $I_{Ca,L}$ recording, $K^+$ in pipette and Tyrode solution was replaced by CsCl. $I_{Na}$ was recorded under conditions of $K^+$-free and a symmetrical $Na^+$ (5 mM) in pipette and superfusion solutions as described previously (Li et al., 2002a).

Acacetin was initially isolated and purified from the TCM Xuelianhua (*Saussurea tridactyla*), and then synthesized in the laboratory as the described above in the section of chemical study on compound A. A 100 mM stock solution of acacetin or its derivative/analogue was made in DMSO, and stored at 4° C.

1.5. Data Acquisition and Analysis

A small aliquot of the solution containing the isolated cells was placed in an open perfusion chamber (1-ml) mounted on the stage of an inverted microscope. Myocytes were allowed to adhere to the bottom of the chamber for 5-10 min and were the superfused at 2-3 ml/min with Tyrode solution. Only quiescent rod-shaped cells with clear cross-striations were used. The studies were conducted at room temperature (21-22° C.) for current recording or 36° C. for action potential recording.

The whole-cell patch-clamp technique was used for electrophysiological recording. Borosilicate glass electrodes (1.2-mm OD) were pulled with a Brown-Flamming puller (model P-97, Sutter Instrument Co, Novato, Calif., USA) and had tip resistances of 2-3 MΩ when filled with pipette solution. Membrane currents were recorded in voltage-clamp mode using an EPC-9 amplifier and Pulse software (HEKA, Lambrecht, Germany). A 3-M KCl-agar salt bridge was used as reference electrode. The tip potentials were compensated before the pipette touched the cell. After a giga-ohm seal was obtained, the cell membrane was ruptured by gentle suction to establish the whole-cell configuration. The cell membrane capacitance (pF) was directly measured using the lock-in module of the Pulse software, and used for normalizing the current in individual cells. The series resistance ($R_s$) was 3-5 MΩ and was compensated by 50-70% to minimize voltage errors. Perforated patch configuration was used for recording action potential in human atrial cells and $I_{Ks}$ in HEK 293 cells as described previously (Li et al., 2002b; Dong et al., 2006). Current signals were low-pass filtered at 5 kHz and stored on the hard disk of an IBM compatible computer.

1.6. Isolated Rabbit Heart Preparations

New Zealand White rabbits of either gender (2-3 kg) were anesthetized with pentobarbital (30 mg/kg, i.v.), and their hearts were quickly removed and placed in oxygenated Tyrode solution, Hearts were mounted on a Langendorff system and perfused with 37° C. oxygenated (95% $O_2$-5% $CO_2$) Tyrode solution containing (in mM) 129 NaCl, 3.0 KCl, 1 $MgCl_2$, 1.5 $CaCl_2$, 20, $NaHCO_3$, 0.9 $NaH_2PO_4$, 10 glucose (pH 7.3-7.4). ECG was recorded with a Powerlab recording system via two electrodes placed respectively on base and apex of the heart. The averaged QT interval from three measured Q-T intervals of rabbit heart ECG was corrected by heart rate (Q-Tc interval) according to the Van de Water's formula: QTc=QT-87×[(60/heart rate)−1] as described previously (Spence et al., 1998).

1.7. Whole Animal Experiments

The study conforms with the Guide for the Care and Use of Laboratory Animals published by the US National Institutes of Health (NIH Publication No. 85-23, revised 1996), and approved by the Institutional Ethic Committee.

1.7.1 In Vivo Electrophysiology in Anesthetized Dogs.

Adult mongrel dogs (12-15 kg) were anesthetized with pentobarbital (30 mg/kg i.v.), supplemented during the experiment when needed. The animal was intubated and ventilated with room air. Body temperature was maintained at 37-38° C. with a temperature control system. The left femoral vein was cannulated for maintenance of anesthesia and introducing the mono-phasic action potential (MAP) recording- and pacing-catheters (Boston Scientific Ltd) to the right atrium. The vagus nerves were isolated and divided in the neck. To block cardiac β-adrenergic effects, nadolol was administered at 0.25 mg/kg i.v., followed by 0.125 mg/kg i.v. every 2 h. A left thoracotomy was performed in the fourth intercostal space, and the pericardium was incised to provide access to the left atrium for introducing the MAP catheter. The catheters were used for recording MAPs of right and left atria, respectively, and for measurement of effective refractory period (ERP). In addition, a plastic tube (~0.8×12 cm) was introduced to the intraduodenum through the pylorus from stomach for drug administration, because acacetin is not water soluble for injection application. A ligation was made at the pylorus with a thick cotton thread to prevent the possible back flow of the duodenum content.

Following a 30-min equilibration period and measurement of atrial excitation threshold with 2-ms duration of stimuli, atrial ERP was determined using a train of 8 basic stimuli (S1, twice-diastolic threshold) followed by an identical premature stimulus (S2). The basic cycle lengths (BCL) of 200, 250 and 300 ms were applied in both right and left atria. S2 was initially delivered late in diastole in 5-ms decrements until a response was not elicited by the S2 indicated on the MAP recording. The ERP was defined as the longest S1-S2 interval failing a propagated response, and the procedure was repeated for three times for each measurement. MAP, ECG and blood pressure signals were continuously monitored and stored on an IBM compatible PC computer using a multiple channels data acquisition system (RM-6280C, Chengdu Instrument Ltd, Chendu, China).

After the measurement of ERP of both right and left atria, 10% PVP 400 (Sigma-Aldrich, 20 ml with 2 ml DMSO) as vehicle control or 20 ml 10% PVP 400 containing 5 mg/kg acacetin (treatment group) or 20 ml 10% PVP 400 containing 5 mg/kg sotalol (positive control) was injected into the duodenum via the drug administration tube. The ERP measurement was then repeated every hour post drug administration for 6 hours. Excitation threshold of both right and left atria was verified before ERP each measurement.

1.7.2. Experimental AF in Anesthetized Dogs.

Vagal nerve plays an important role in genesis of AF (Chiou et al., 1997; Zipes et al., 1974; Liu and Nattel, 1997), and therefore, vagotonic AF model is generally employed to investigate AF and anti-fibrillation. Sustained vagotonic AF was generated in anesthetized dogs by introducing two MAP catheters respectively into the right atrium and the left ventricle along with stimulation of the divided bilateral vagal nerves in the neck. The vagal nerves were stimulated using a bipolar electrodes with 15 Hz, 0.2 ms duration voltage step (60% threshold) to induce a 75% reduction of heart rate. Ventricular pacing was performed with 2 ms voltage pulses (2.5 Hz, 150% diastolic threshold) when vagal nerves were continuously stimulated. AF was generated by the BCL 100-ms S1 followed by S2, lasting for 10 min. No AF occurrence or shortened AF duration during the continuous vagal stimulation was considered to be effective prevention of AF at certain time points of AF generation during 0.5-4 h post intraduodenal drug administration. The sustained AF could be repeatedly generated and terminated by stopping vagal stimulation. AF incidence and AF duration were recorded before and at different time points (0.5, 1, 1.5, 2, 3, and 4h) after intraduodenal administration of drugs.

1.8. Acute Toxicity Assessment.

The acute toxicity of acacetin was determined in Kunmin mice (18-20 g, 50% female and 50% male). The maximum concentration stock (263 mg/ml) of acacetin was prepared in DMSO, and then mixed with 10% PVP 400 to make acacetin suspension for oral administration. The animals were observed closely with a two-week duration for death number and activity.

1.9. Statistical Analysis

Group data are expressed as mean±S.E.M. Statistical analysis was performed using Student's t-test for paired or unpaired observations to evaluate significant differences between two group means, and ANOVA for multiple groups. Quantitative data were analyzed using the Fisher exact test. A two tailed P<0.05 was taken to indicate a statistical significant difference. Nonlinear curve fitting was performed using Pulsefit (HEKA) and Sigmaplot (SPSS, Chicago, Ill.).

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1

Figure 2A:
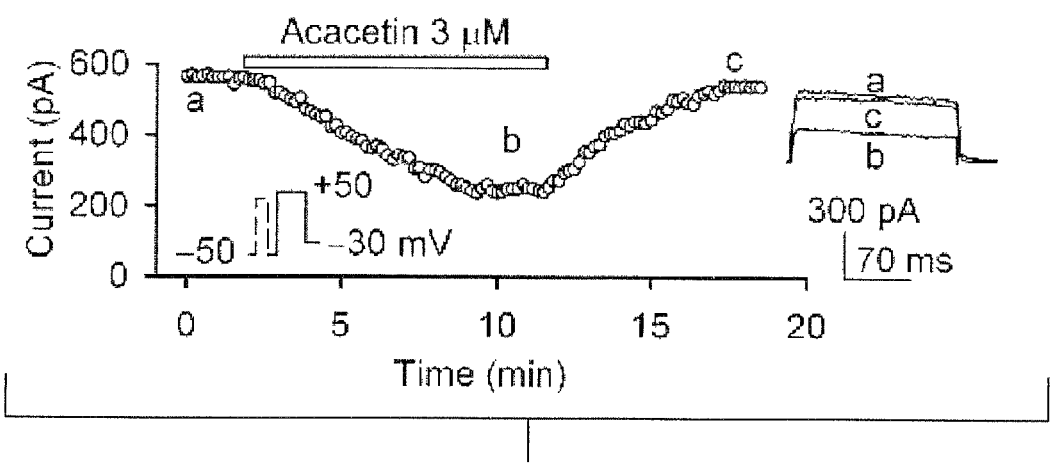
FIGS. 2A, 2B, and 2C show the effects of acacetin on $I_{Kur}$.
Figure 2B:
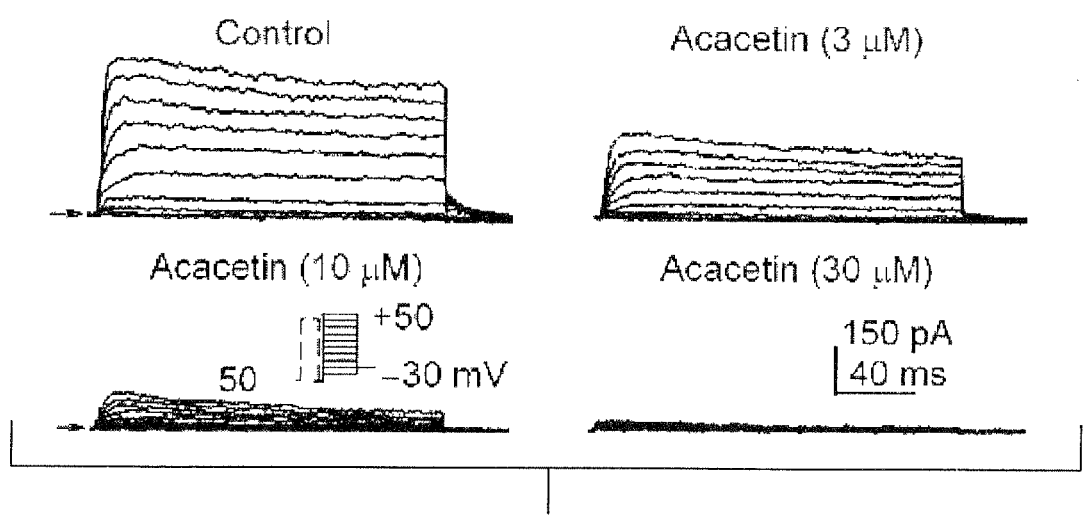
Figure 2C:
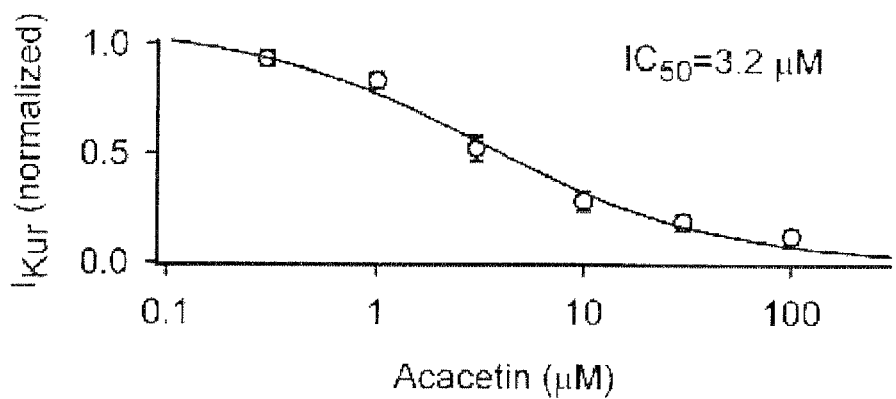

Effects of acacetin on $I_{Kur}$, $I_{to}$, and action potential in human atrial myocytes To determine the effects of acacetin on $I_{Kur}$, the time course of the current was recorded in a representative human atrial cell using a 100-ms prepulse to +40 mV to partially inactivate $I_{to}$, followed by 160-ms test pulses from −50 to +50 mV after a 10-ms interval, then to −30 mV (Tian et al., 2006; Gao et al., 2004) in the absence and presence of acacetin (FIG. 2A). Acacetin at 3 µM gradually inhibited $I_{Kur}$ with 8 min exposure, and the effect recovered (by 94%) on washout. FIG. 2B shows the voltage-dependent $I_{Kur}$ elicited by voltage protocol shown in the inset. Acacetin at 3, 10, and 30 µM substantially inhibited both tail and step currents of $I_{Kur}$. The concentration-response relationship for the inhibition of $I_{Kur}$ by acacetin from 0.3 to 100 µM was evaluated at +40 mV (FIG. 2C). Data were fitted to the Hill equation: $E=E_{max}/[1+(IC_{50}/C)^b]$, where E is the inhibition of the current in percentage at concentration C, $E_{max}$ is the completed inhibition, $IC_{50}$ is the concentration for a half-maximum action, and b is the Hill coefficient. The $IC_{50}$ of acacetin for inhibiting $T_{Kur}$ was 3.2 µM, and its Hill co-efficient was 0.8.

Figure 3A:
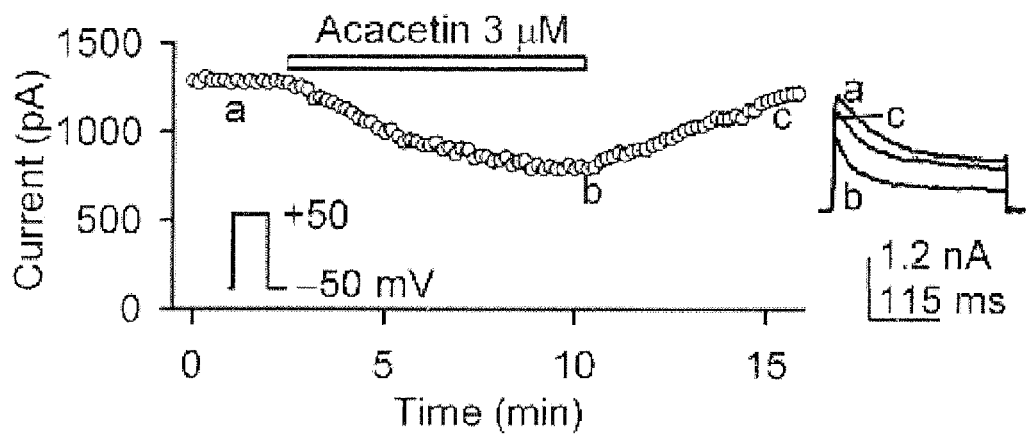
FIGS. 3A, 3B, 3C show the effect of acacetin on $I_{to}$ in human atrial myocytes.
Figure 3B:
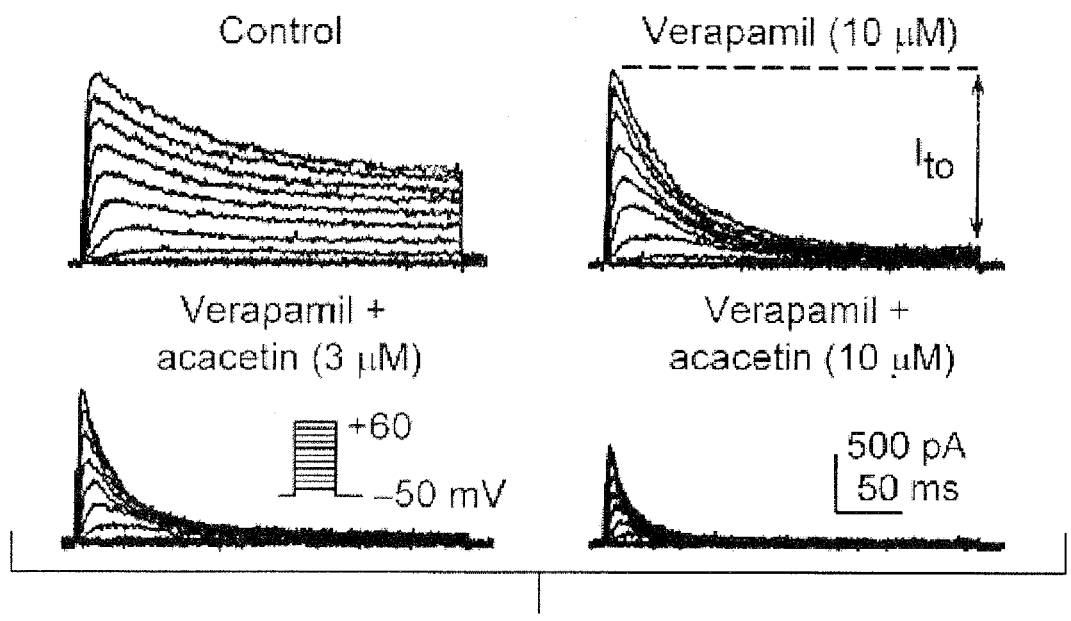
Figure 3C:
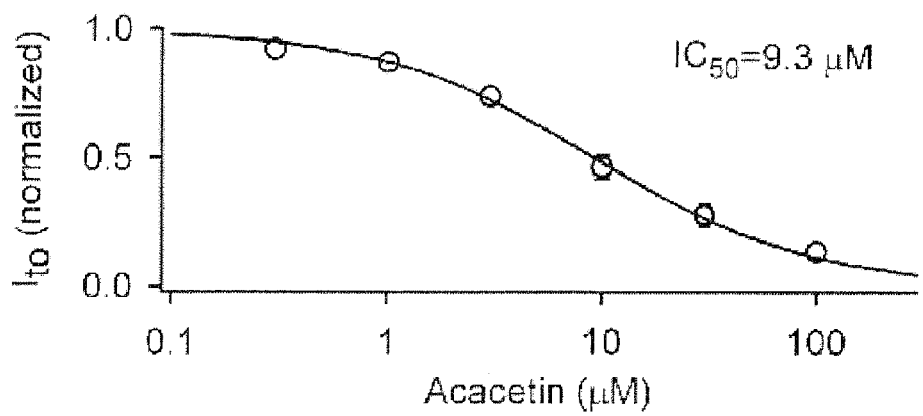

To examine the effect of acacetin on $I_{to}$, the time course of $I_{to}$ was recorded in a typical experiment in the absence and presence of acacetin (FIG. 3A). Acacetin at 3 µM reduced $I_{to}$, and the effect recovered (by 95%) on washout. However, the sustained current (i.e. $I_{Kur}$) was simultaneously reduced by acacetin. Although the $I_{to}$ measured was peak to the 'quasi'-steady-state level, we suspected that the evaluation of the effect of acacetin on $I_{to}$ might not be accurate. We have recently found that verapamil inhibits $I_{Kur}$ without reduction of $I_{to}$ amplitude, while it induces an increase of measured $I_{to}$ in human atrial myocytes (Gao et al., 2004). Therefore, verapamil at 10 µM was used to separate $I_{to}$ as shown in FIG. 3B. $I_{to}$ amplitude was actually increased by verapamil. Voltage-dependent $I_{to}$ was substantially inhibited by 3 and 10 µM acacetin (FIG. 3B). The inhibitory effect of $I_{to}$ by acacetin was concentration-dependent with an $IC_{50}$ of 9.3 µM (FIG. 3C), and a Hill co-efficient of 0.9.

Figure 4A:
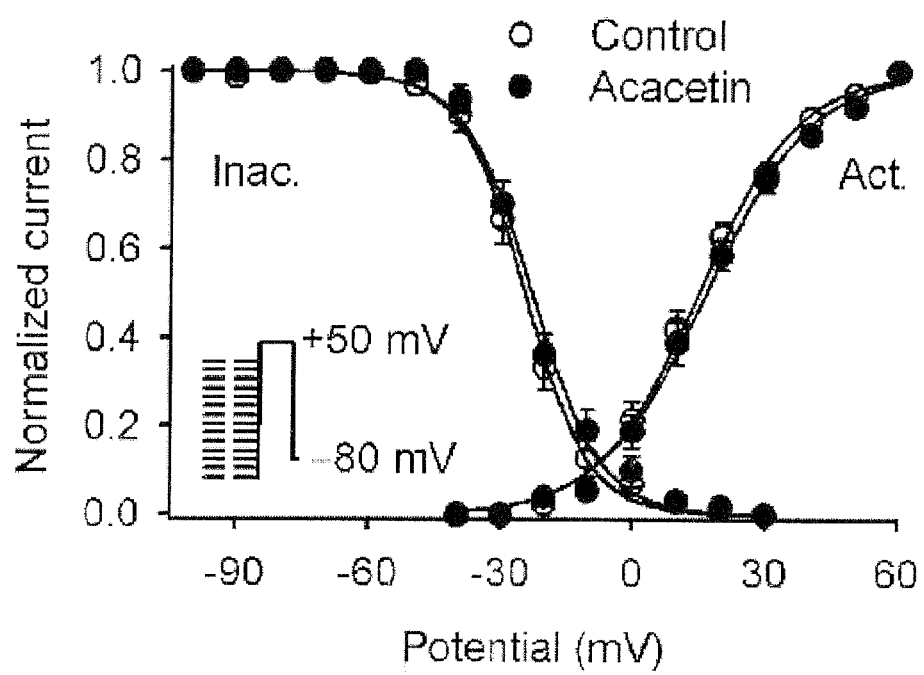
FIGS. 4A and 4B show the effects of acacetin on kinetics of $I_{to}$.
Figure 4B:
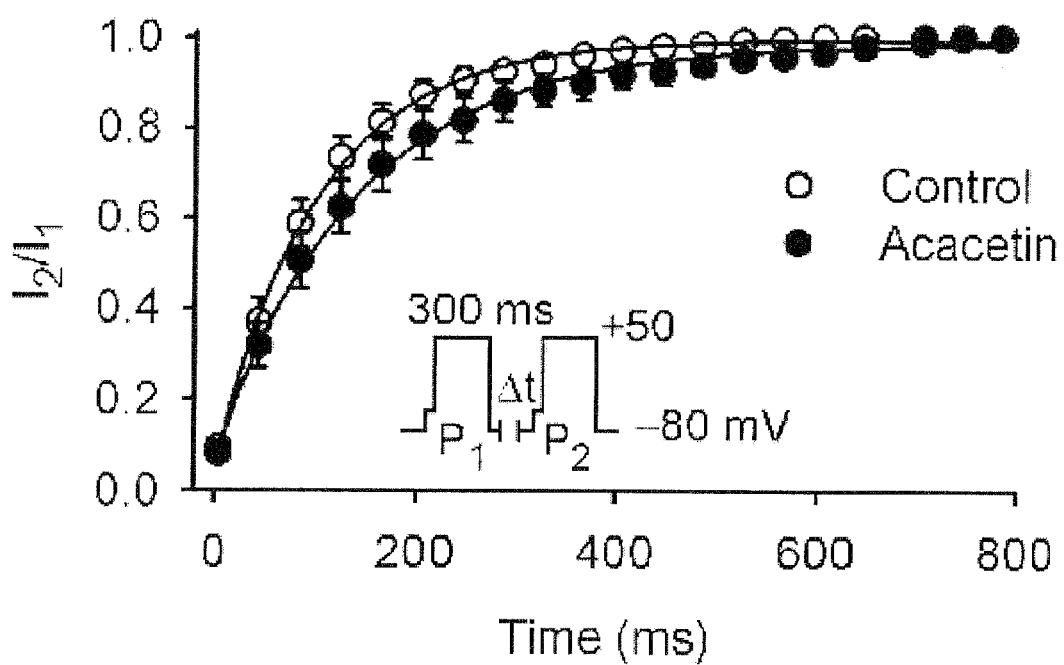

Acacetin at 10 µM did not affect voltage-dependence of the steady-state inactivation and activation of $I_{to}$ (FIG. 4A). However, acacetin at 10 µM significantly increased the recovery time constant of $I_{to}$ (τ: 102+12 ms in control; 136±17 ms in acacetin, P<0.01) (FIG. 4B), suggesting that acacetin slows the recovery of $I_{to}$ from inactivation.

Figure 5A:
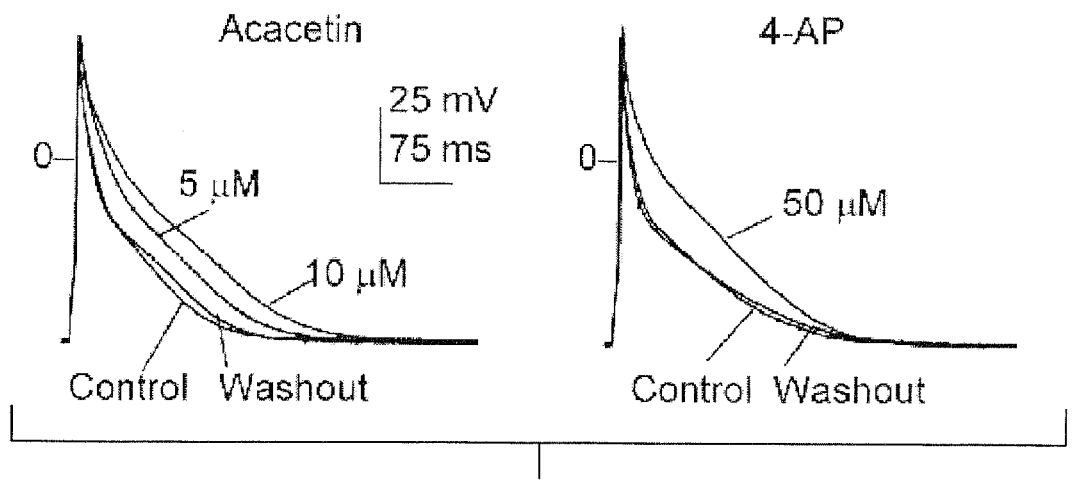
FIGS. 5A, 5B, and 5C show the effect of acacetin on action potential in human atrial myocytes.
Figure 5B:
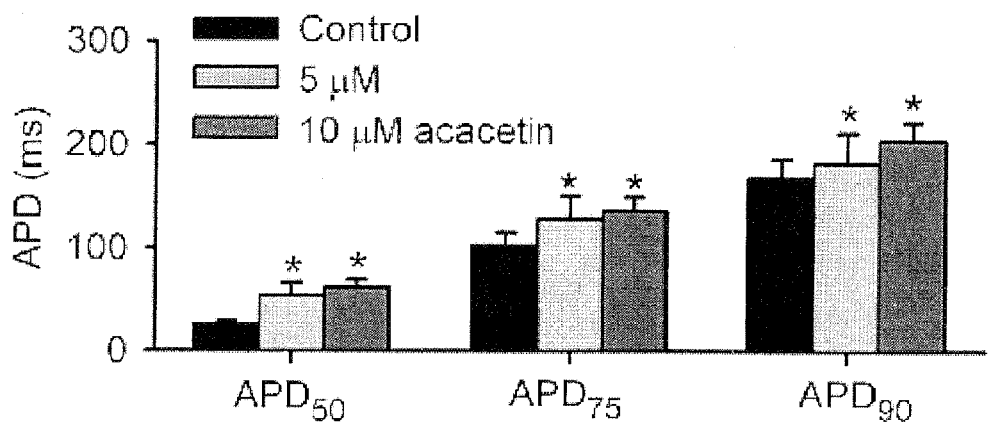
Figure 5C:
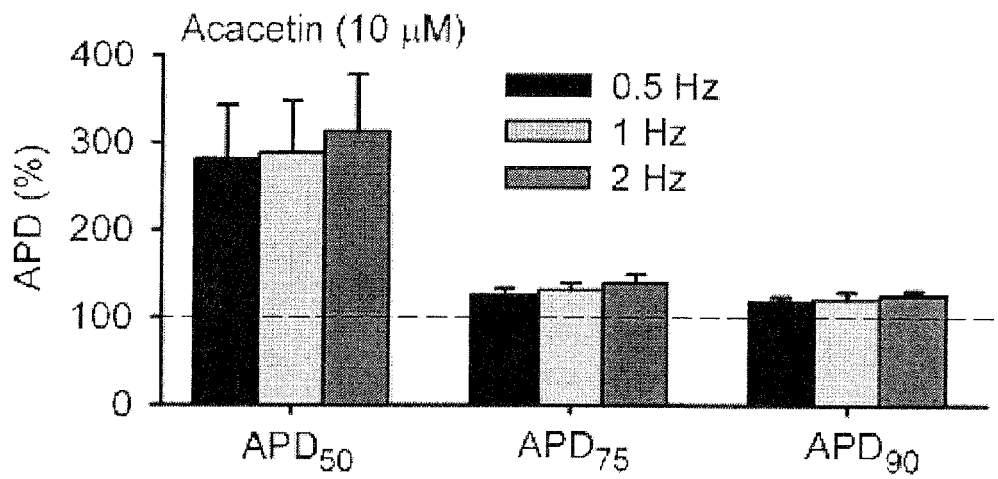

The inhibition of $I_{Kur}$ and $I_{to}$ by acacetin suggests that this compound prolongs the action potential duration (APD) in human atrial myocytes. We therefore recorded action potentials at 36° C. with the perforated patch configuration in current clamp mode to determine the effect of acacetin on human atrial APD. FIG. 5A illustrates action potentials recorded at 2 Hz in representative human atrial myocytes in the absence and presence of acacetin or 4-AP (a well-known blocker of $I_{Kur}$) (Li et al., 1996b). Acacetin at 5 or 10 µM prolonged the APD in a parallel fashion without affecting the resting membrane potential or the amplitude of action potential. This effect recovered on washout. The APD at 50%, 75%, and 90% repolarization was increased significantly (FIG. 5B). Acacetin induced a slight rate-dependent increase in $APD_{50}$, $APD_{75}$ and $APD_{90}$. 4-AP at 50 μM prolonged $APD_{50}$ more than $APD_{90}$ (right panel of FIG. 5A), and induced a reverse rate-dependent prolongation of $APD_{50}$, $APD_{75}$ and $APD_{90}$ (data not shown). These results suggest that the prolongation of human atrial APD by acacetin is likely not limited to the inhibition of $I_{Kur}$ and $I_{to}$.

Example 2

Figure 6C:
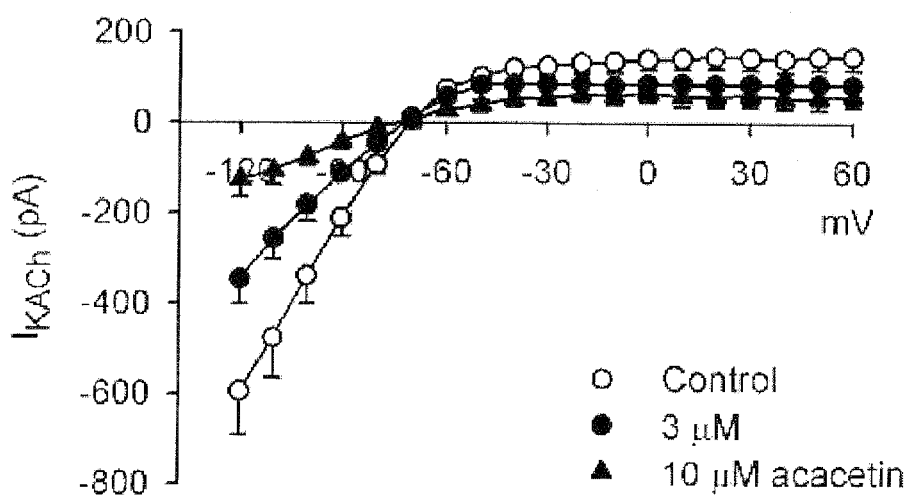
Figure 7A:
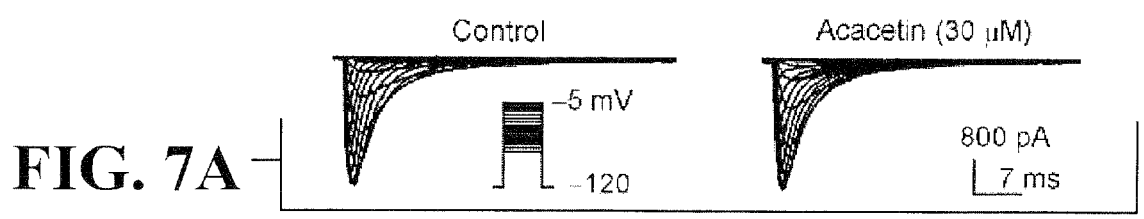
FIGS. 7A-7F show no effects of acacetin on $I_{Na}$, $I_{Ca.L}$, and $I_{K1}$ in guinea pig ventricular myocytes.
Figure 7B:
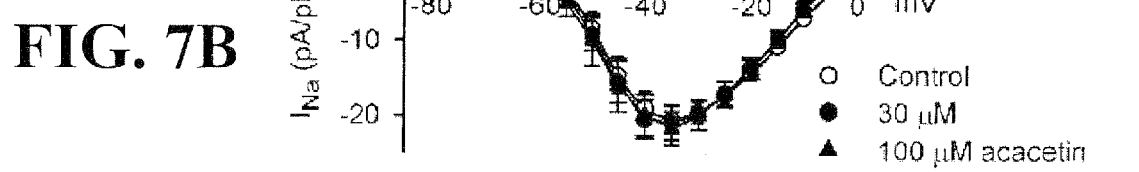
Figure 7C:
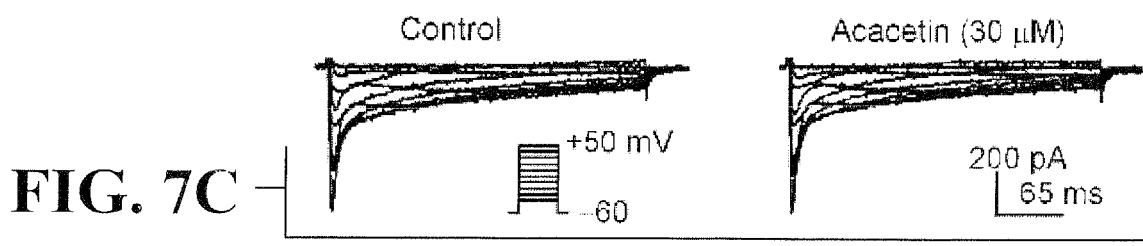
Figure 7D:
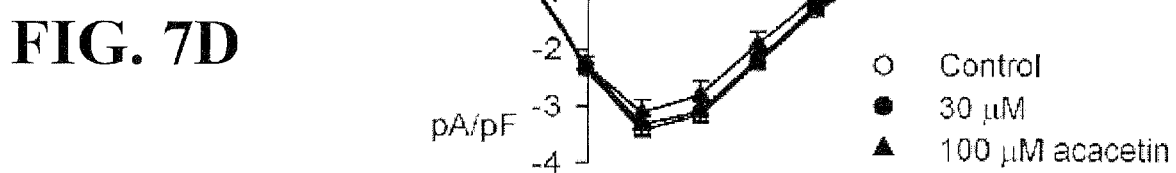
Figure 7E:
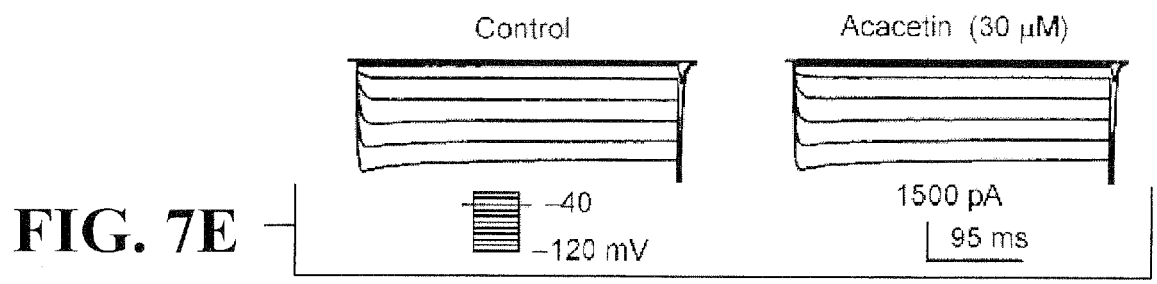
Figure 7F:
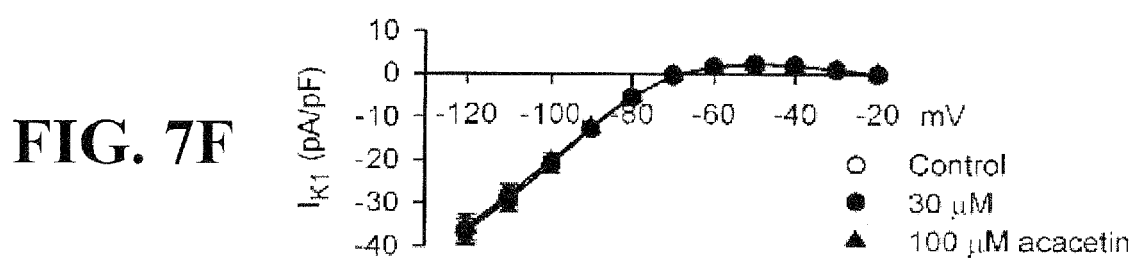

Effects of Acacetin on Acetylcholine-Activated Potassium Currents in Guinea Pig Atrial Myocytes The effects of acacetin on acetylcholine-activated ($I_{K.ACh}$) were studied in left atrial myocytes from guinea pig atrial myocytes, because of no expression of $I_{Kur}$ (Kv1.5) and $I_{to}$ channels in atria of this species. The membrane currents recorded with a ramp protocol (FIG. 6A) and voltage step protocol (FIG. 6B) showed that carbachol at 5 μM augmented membrane conductance, and acacetin at 3 μM significantly reversed the increased conductance. FIG. 6C displays I-V relationships of carbachol-evoked $I_{K.ACh}$ obtained by digital subtraction of currents before and after carbachol and carbachol plus acacetin. Acacetin at 3 and 10 μM substantially blocked $I_{K.ACh}$ (P<0.0 at −100 to −80 mV and +50 to +60 mV. At test potentials of −100 and +50 mV, $I_{K.ACh}$ was reduced from −338.3±61.5 pA and 147.2, 30.1 of control to −180.2±36.7 and 87.8±36.1 pA with 3 μM acacetin (P<0.01, n=5), and −75.6±21.1 and 55.7±26.2 pA with 10 μM acacetin (P<0.01, n=6).

Example 3

Effects of Acacetin on Other Cardiac Ionic Currents

The effects of acacetin on other cardiac ionic currents, e.g. $I_{Na}$, $I_{Ca.L}$, and $I_{K1}$, were studied in guinea pig ventricular myocytes. FIG. 7 illustrates the results of recordings for $I_{Na}$, $I_{Ca.1}$, and $I_{K1}$ in different cells using the voltage protocols shown in the insets. Acacetin at 30 and 100 μM had no effect on $I_{Na}$, $I_{Ca.L}$, or $I_{K1}$.

Figure 8A:
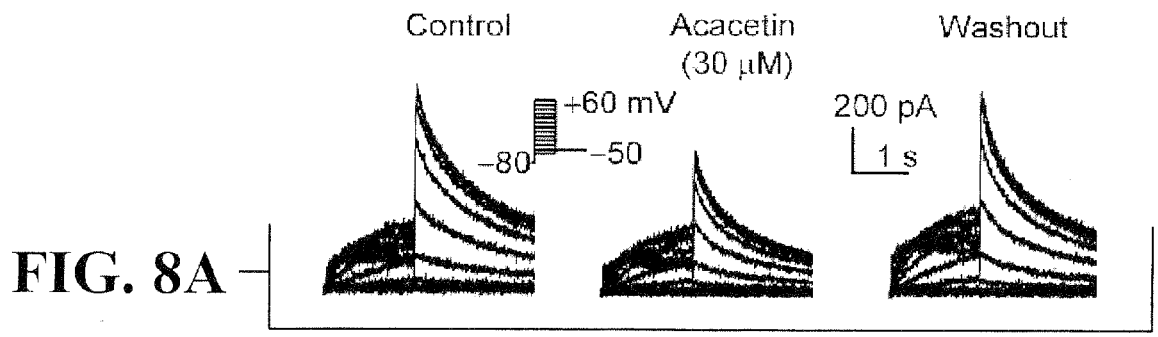
FIGS. 8A, 8B, 8C, and 8D show the effects of acacetin on $I_{hERG}$ and $I_{Ks}$ stably expressed in HEK 293 cells.
Figure 8B:
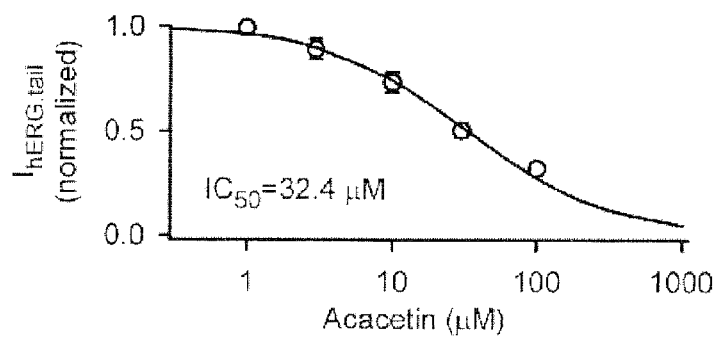

The effect of acacetin on $I_{Kr}$ or $I_{Ks}$ was determined in HEK 293 cells stably expressing hERG channels (α-subunit of human cardiac $I_{Kr}$) or $I_{Ks}$ channels (hKCNQ1/hKCNE1). Acacetin at 30 μM inhibited the amplitude of hERG channel currents elicited by the voltage protocol (inset, FIG. 8A) in a representative cell, and the effect disappeared on washout (FIG. 8A). The $IC_{50}$ of acacetin for inhibiting $I_{hERG.tail}$ was 32.4 μM (FIG. 8B), and its Hill co-efficient was 0.9.

Figure 8C:
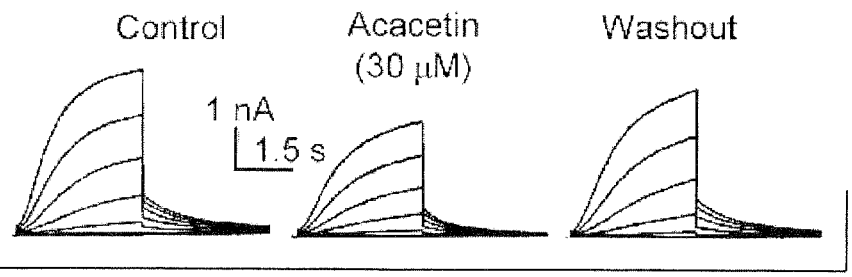
Figure 8D:
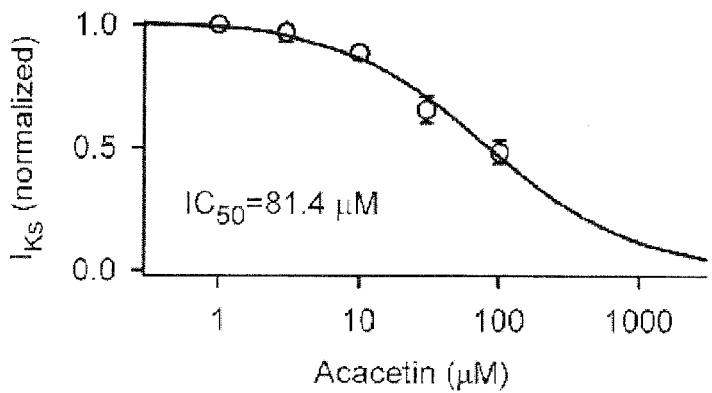

FIG. 8C displays the effects of acacetin on $I_{Ks}$ stably expressed in an HEK 293 cell line. Acacetin at 30 μM significantly inhibited the amplitude of $I_{Ks}$, and the effect partially recovered (by 83%) on washout. Acacetin decreased $I_{Ks}$ at +20 to +60 mV in a concentration-dependent manner. The $IC_{50}$ of acacetin for inhibiting $I_{Ks}$ (+40 mV) was 81.4 μM (FIG. 8D), and its Hill co-efficient was 0.8.

Example 4

Effects of Acacetin on QTc Interval of ECG in Isolated Rabbit Hearts

Figure 9A:
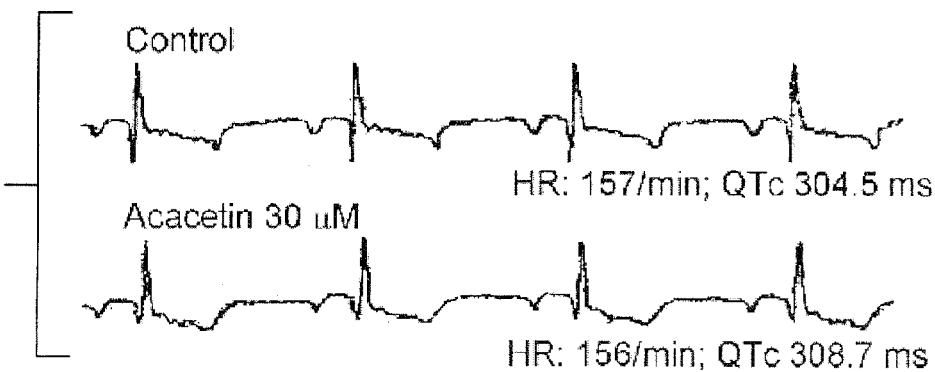
FIGS. 9A, 9B, 9C, and 9D show the effects of acacetin and quinidine on heart rate and QTc interval of ECG in isolated rabbit hearts.
Figure 9B:
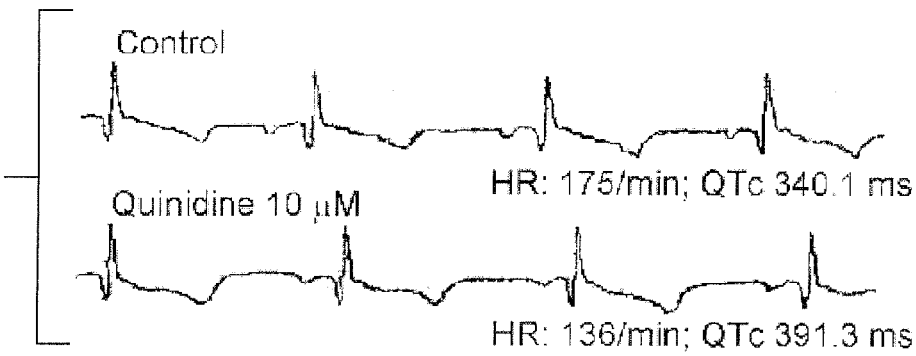
Figure 9C:
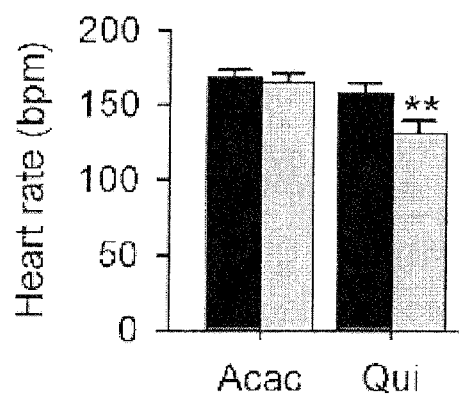
Figure 9D:
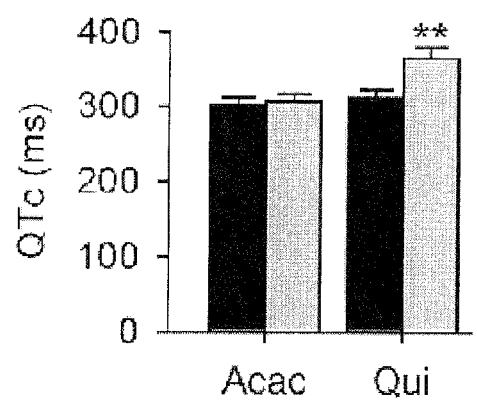

The above results for the inhibition of $I_{hERG}$ and $I_{Ks}$ suggest that acacetin likely has the potential to prolong QT interval of ECG. Rabbit hearts express significant $I_{Kr}$ channels (Salata et al., 1996), and have been used for evaluating proarrhythmia of cardiac active agents (Milberg et al., 2004; Weissenburger et al., 1993; Cahill and Gross, 2004). Therefore the isolated rabbit heart was employed to study whether or not acacetin would increase QTc. The hearts were perfused using a hypokalemic (3 mM K+) solution. Representative ECG recordings are shown in FIG. 9A for acacetin and FIG. 9B for quinidine. Acacetin at 30 μM had no effect on heart rate or the QTc interval of the ECG, while quinidine at 10 μM slowed heart rate and significantly increased QTc interval. Mean values of heart rate and QTc interval of ECG are illustrated in FIGS. 9C & 9D. These results suggest that acacetin does not prolong the QTc interval of the ECG of the isolated rabbit heart under hypokalemic conditions.

Example 5

Effects of Acacetin on Atrial Refractory Period in Anesthetized Dogs

Figure 10A:
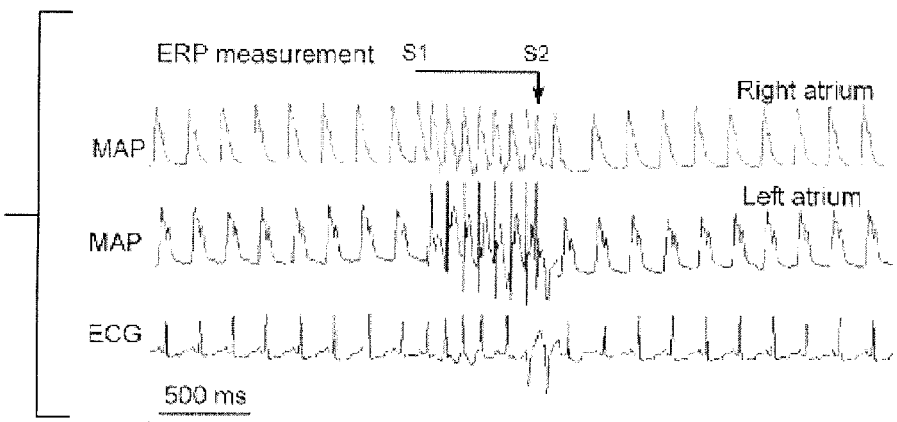
FIGS. 10A, 10B, and 10C show the mono-phasic action potentials (MAPs) used to measure left and right atrial ERP and S2-induced AF is prevented by acacetin in anesthetized dogs.
Figure 10B:
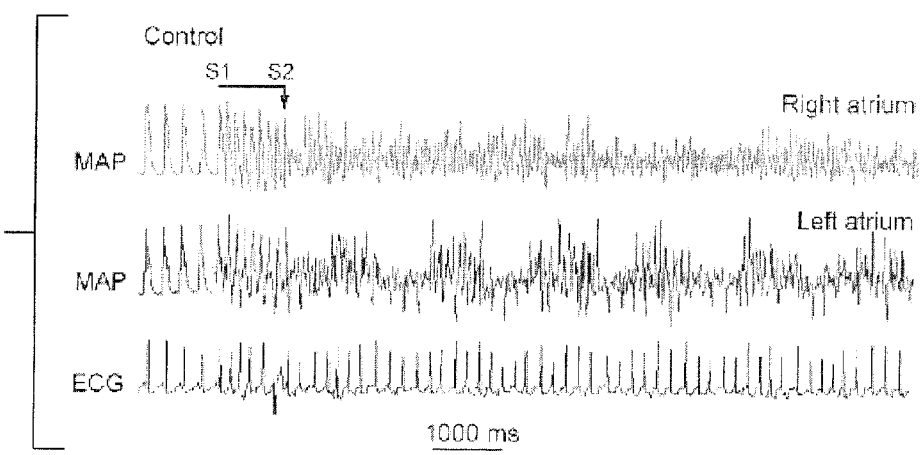
Figure 10C:
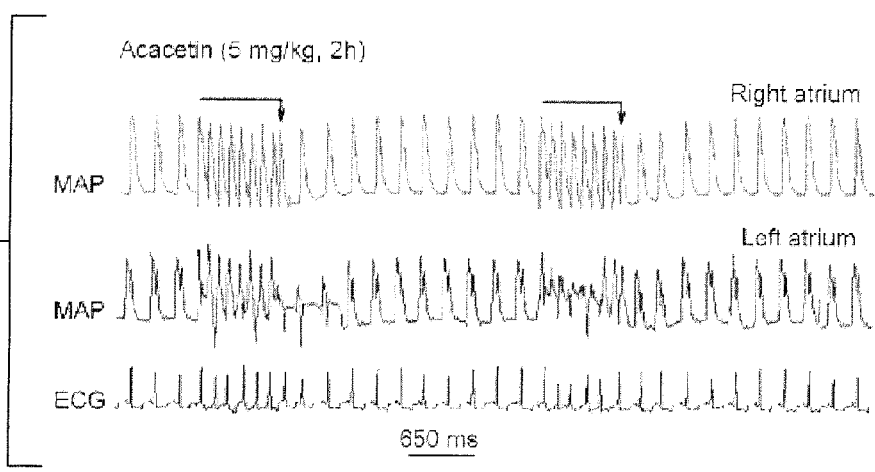

The ERPs were determined in anesthetized dogs using the BCLs of 300, 250, and 200 ms by introducing S1-S2 via a programmed cardiac stimulator (FIG. 10A). We found that left and right atrial ERP was significantly prolonged after the duodenal administration of acacetin (5 mg/kg) or sotalol (5 mg/kg) during a 4-hour observation at basic cycle lengths (BCL) of 300, 250, and 200 ms (Tables 1 and 2). FIG. 11A shows an example of mean values of the percent changes in left atrial ERP. Atrial ERP was increased by 10 to 25% in the drug administration groups, but not in the vehicle control group S2 was found to trigger sustained AF (lasting >1 min) when right ERP was measured with 200 ms BCL in anesthetized dogs. In one animal from the acacetin group, AF was induced by S2 before drug administration (FIG. 10B), but not after two hours of acacetin administration (FIG. 10C). In another animal from the vehicle group, AF was always induced by S2 when right atrial ERP was determined during the observation period. This suggests that acacetin likely has an anti-AF effect.

Sotalol at 5 mg/kg showed a reverse rate-dependent prolongation of ERP and increased QTc interval as reported previously (Nademanee, 1992; Roden, 1993). However, acacetin had no such reverse rate-dependent effect on ERP (FIG. 11B), and did not prolong QTc interval (FIG. 11C). These results suggest that acacetin is likely an anti-AF agent without causing QTc prolongation.

Example 6

Effects of Acacetin on Atrial Fibrillation in Anesthetized Dogs

Figure 12A:
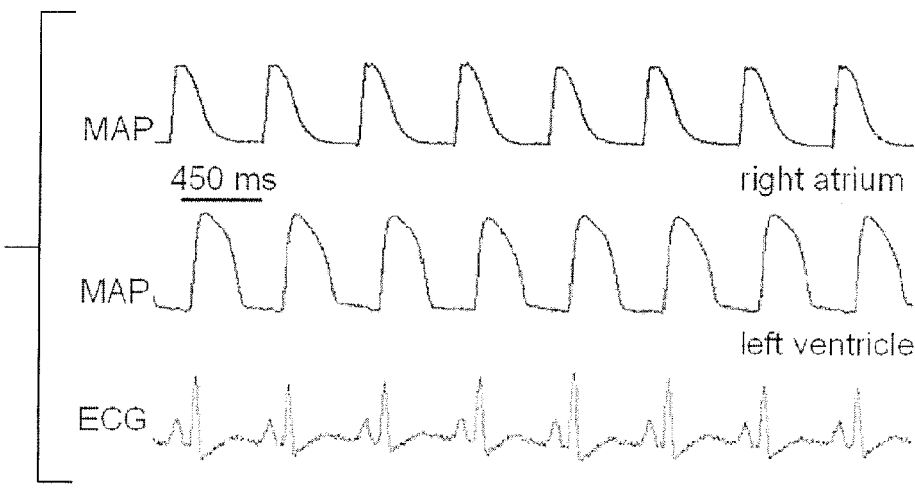
FIGS. 12A and 12B show the AF induction in anesthetized dogs.
Figure 12B:
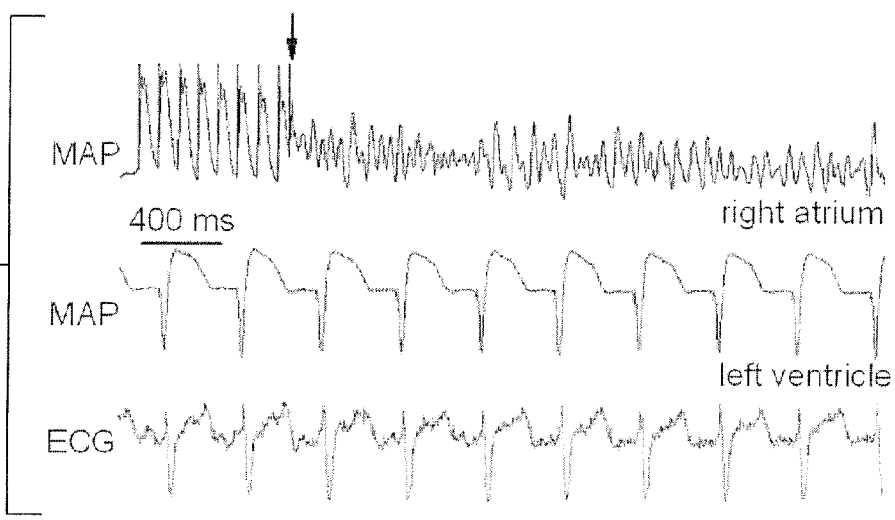
Figure 13A:
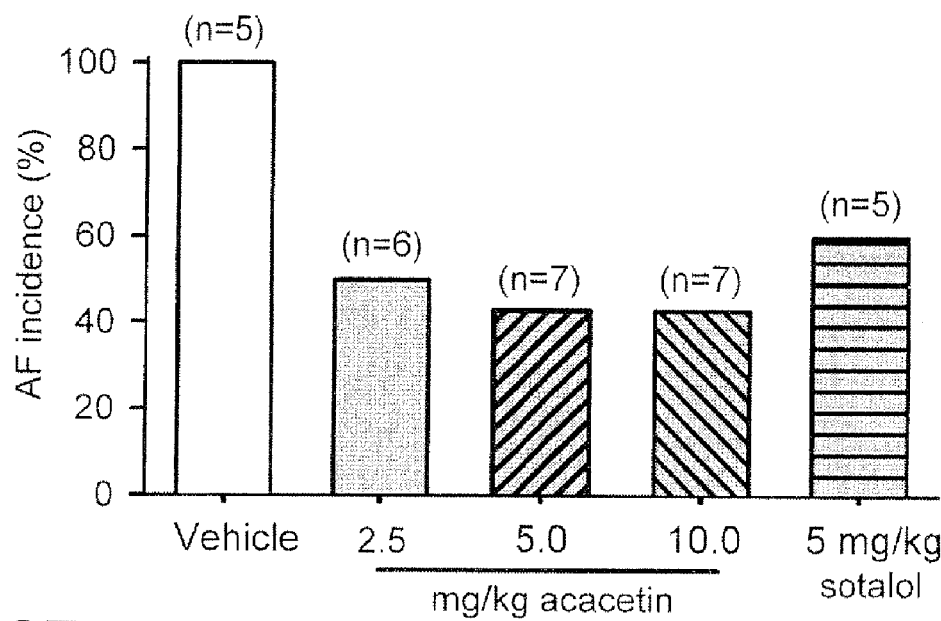
FIGS. 13A and 13B show the incidence of AF and drugs effects on the AF induction in anesthetized dogs.

The effect of acacetin on experimental AF was then evaluated in anesthetized dogs. AF was induced by S1-S2 stimulation at 100 ms BCL with bilateral vagal stimulation (see Methods & FIG. 12) at certain time points during the 0.5 to 4 h period following intraduodenal administration. AF lasted for 10 min and terminated once vagal stimulation was stopped. No AF occurrence or shortened AF duration during the continuous vagal stimulation were considered to represent prevention of AF. The incidence of AF was reduced in drug treatment groups (FIG. 13A). Sustained AF was observed in 100% of animals (n=5) at each AF induction test in the vehicle group, but not in 50% (3 of 6), 57% (4 of 7), and 57% (4 of 7) of the animals in the 2.5, 5, and 10 mg kg acacetin groups, and 40% (2 of 5) of animals in the sotalol group (5 mg kg).

Figure 13B:
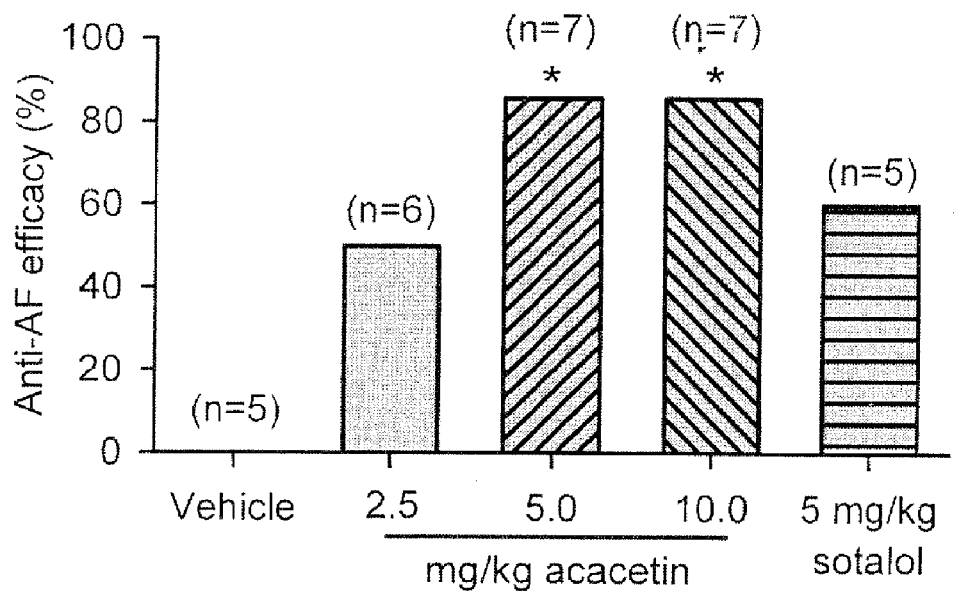

In addition, in the 5 mg/kg acacetin group, two dogs showed a shorter duration of AF (one lasted for 5 min and 31 s, and another lasted for 6 min 12 s) two hours after drug administration. In the 10 mg/kg acacetin group, AF lasted for 4 min and 30 s in one animal, and 7 min and 11 s in another animal. In the sotalol group, shortened AF duration (of 8 min and 5 s) was observed in one animal. The summarized anti-AF efficacy was 0%, 50%, 85.7%, 85.7%, and 60% in the vehicle group, 2.5 mg/kg acacetin group, 5 mg/kg acacetin group (P<0.05), 10 mg/kg acacetin group (P<0.05), and 5 mg/kg sotalol group, respectively (FIG. 13B). These results indicates that acacetin prevents AF induction in anesthetized dogs.

Example 7

Acute Toxicity in Mice

Acute in vivo toxicity was assessed in mice with a maximal concentration of acacetin obtainable in suspension of a maximal volume after starvation of the animal for 14 h. The dose of 0.3 g/kg acacetin was administered three times at intervals of 1.5 h. No animal death occurred within a two-week observation period, and there was no abnormal activity compared to vehicle-control animals. This result suggests that oral administration of acacetin has low or no acute toxicity.

Example 8

Comparative Study Upon the Effects of Acacetin and its Derivatives/Analogs on Kv1.5 and hERG Channels The comparative study upon the effects of acacetin and its derivatives/analogs on Kv1.5 and hERG channels were performed in HEK 293 cells stabling expressing these channel genes, respectively. As Table 3 shows, the $IC_{50}$ (3.4 µM) of acacetin for blocking Kv1.5 channels is close to that (3.2 µM) of human atrial $I_{Kur}$ (FIG. 2). Although the derivative A-2 has a smaller $IC_{50}$ (2.04 µM) for blocking Kv1.5 channels, the blockade of hERG channels is also stronger than that of acacetin. The $IC_{50}$s of A-4, A-5, and A-6 are larger than that of acacetin. Other derivatives/analogs studied have no effect or a week inhibitory effect on Kv1.5. These results indicate that the acacetin is all ideal compound to develop for the anti-AF study in humans, although a possible better effect from other derivatives/analogues can not be excluded.

Example 9

Preparation of Acacetin and its Derivatives

Synthesis of Acacetin
Reaction Scheme:

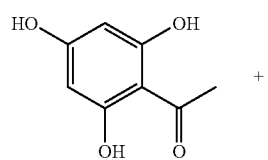

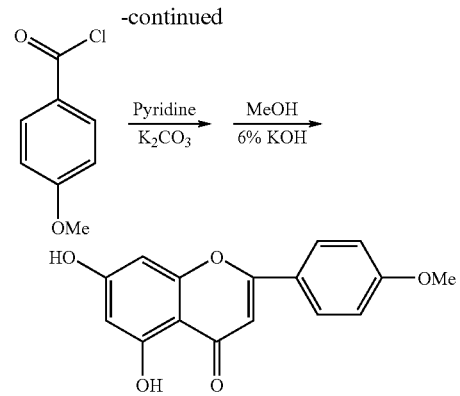

Operation Process.

To a solution of 80 ml dry pyridine was added 9.62 g 2',4',6'-trihydroxyacetophenone and 30 g anhydrous $K_2CO_3$ and 31 g 4-methoxybenzoyl chloride successively, then extracted reaction solution with chloroform when it was refluxed 3 hours at 120° C. by oil bath, and washed the chloroform extraction by water (100 ml), the chloroform was dried by anhydrous $K_2CO_3$ and decoloured by active carbon, then concentrated it in vacuo. The residue was dissolved with 60 ml anhydrous ethanol, and have deposition in solution, filtered it, afforded 13.53 g intermediate.

To a solution of 50 ml methanol was added 6.3 g above intermediate and 6% KOH solution, stirred and refluxed it 20 hours, then recovered most of methanol in vacuo, and extracted it with chloroform to remove some extraneous component, the deposit was obtained after the water phase was acidified pH 9 by 10% acetic acid, and filtered it, washed by water, dried it, 1.83 g acacetin was obtained at last.

Preparation of A-02-11-11

To a 0.75 ml pyridine was added 30 mg acacetin and 0.50 ml acetic anhydride, stirred it 2 hours at room temperature, the residue was chromatographed, and eluted with petrol ether: acetone=2:1, afforded A-02-1-11.

Preparation of A-02-11-12

To a 0.75 ml pyridine was added 30 mg acacetin and 0.50 ml benzoic anhydride, stirred it 2 hours at room temperature, the residue was chromatographed, and eluted with petrol ether: acetone=2:1, afforded A-02-11-12.

Preparation of A-02-11-13

To a 0.75 ml pyridine was added 30 mg acacetin and several drops methyl iodide, stirred it 2 hours at room temperature, the residue was chromatographed, and eluted with petrol ether: acetone=2:1, afforded A-02-11-13.

Preparation of A-02-11-14

To a 0.75 ml pyridine was added 30 mg acacetin and several drops bromethyl, stirred it 24 hours at room temperature, the residue was chromatographed, and eluted with petrol ether: acetone=2:1, afforded A-02-11-14.

Preparation of A-2 and A-3

To a solution of 80 ml dry pyridine was added 9.62 g 2',4',6'-trihydroxyacetophenone and 30 g anhydrous $K_2CO_3$ and 31 g 4-methoxybenzoyl chloride successively, then extracted reaction solution with chloroform when it was refluxed 3 hours at 120° C. by oil bath, and washed the chloroform extraction by water (100 ml), the chloroform was dried by anhydrous $K_2CO_3$ and decoloured by active carbon, then concentrated it in vacuo. The residue was dissolved with 60 ml anhydrous ethanol, and have deposition in solution, filtered it, afforded 13.53 g intermediate. The residue have three spots assayed by TALC, then chromatographed, and eluted with petrol ether: acetone=2:1, afforded A-2 (203 mg), A-3 (50 mg) and acacetin (1.83 g).

Preparation of A-4

To a solution of 0.8 ml dry pyridine was added 100 mg 2'-hydroxyacetophenone and 300 mg anhydrous $K_2CO_3$ and 125 mg 4-methoxybenzoyl chloride successively, then extracted reaction solution with chloroform when it was refluxed 3 hours at 120° C. by oil bath, and washed the chloroform extraction (10 ml) by water (5 ml), the chloroform was dried by anhydrous $K_2CO_3$ and decoloured by active carbon, then concentrated it in vacuo. The residue was dissolved with 3 ml anhydrous ethanol, and have deposition in solution, filtered it, afforded 31 mg A-4.

Preparation of A-5

To a solution of 0.8 ml dry pyridine was added 100 mg 5'-chloro-2'-hydroxyacetophenone and 300 mg anhydrous $K_2CO_3$ and 100 mg 4-methoxybenzoyl chloride successively, then extracted reaction solution with chloroform when it was refluxed 3 hours at 120° C. by oil bath, and washed the chloroform extraction (10 ml) by water (5 ml), the chloroform was dried by anhydrous $K_2CO_3$ and decoloured by active carbon, then concentrated it in vacuo. The residue was dissolved with 3 ml anhydrous ethanol, and have deposition in solution, filtered it, afforded 35 mg A-5.

Preparation of A-6

To a solution of 0.8 ml dry pyridine was added 100 mg 2'-hydroxy-5'-methylacetophenone and 300 mg anhydrous $K_2CO_3$ and 100 mg 4-methoxybenzoyl chloride successively, then extracted reaction solution with chloroform when it was refluxed 3 hours at 120° C. by oil bath, and washed the chloroform extraction (10 ml) by water (5 ml), the chloroform was dried by anhydrous $K_2CO_3$ and decoloured by active carbon, then concentrated it in vacuo. The residue was dissolved with 3 ml anhydrous ethanol, and have deposition in solution, filtered it, afforded 25 mg A-6.

It should be understood that the examples and embodiments described herein are for illustrative purposes only and that various modifications or changes in light thereof will be suggested to persons skilled in the art and are to be included within the spirit and purview of this application

REFERENCES

1. Balser J R, Bennett P B, Hondeghem L M, and Roden D M (1991) Suppression of time-dependent outward current in guinea pig ventricular myocytes. Actions of quinidine and amiodarone. *Circ. Res.* 69:519-529.
2. Benjamin E J, Wolf P A, D'Agostino R B, Silbershatz H, Kannel W B, and Levy D (1998) Impact of atrial fibrillation on the risk of death: the Framingham Heart Study. *Circulation* 98:946-952.
3. Blaauw Y, Gogelein H, Tieleman R G, van Hunnik A, Schotten U, and Allessie M A (2004) "Early" class III drugs for the treatment of atrial fibrillation: efficacy and atrial selectivity of AVE0118 in remodeled atria of the goat. *Circulation* 110:1717-1724.
4. Bosch R F, Zeng X, Grammer J B, Popovic K, Mewis C, and Kuhlkamp V (1999) Ionic mechanisms of electrical remodeling in human atrial fibrillation. *Cardiovasc. Res.* 44:121-131.
5. Brendel J and Peukert S (2003) Blockers of the Kv1.5 channel for the treatment of atrial arrhythmias. *Curr. Med. Chem. Carciovasc. Hematol. Agents* 1:273-287.
6. Burashnikov A, Di Diego J M, Zygmunt A C, Belardinelli L, and Antzelevitch C (2007) Atrium-selective sodium channel block as a strategy for suppression of atrial fibrillation: differences in sodium channel inactivation between atria and ventricles and the role of ranolazine. *Circulation* 116:1449-1457.
7. Cahill S A and Gross G J (2004) Propafenone and its metalbolites preferentially inhibit $I_{Kr}$ in rabbit ventricular myocytes. *J. Pharmacol. Exp. Ther.* 308:59-65.
8. Chiou C W, Eble J N, and Zipes D P (1997) Efferent vagal innervation of the canine atria and sinus and atrioventricular nodes. The third fat pad. *Circulation* 95:2573-2584.
9. Cody V (1988) Crystal and molecular structures of flavonoids. *Prog. Clin. Biol. Res.* 280:29-44.
10. Courtemanche N M, Ramirez R J, and Nattel S (1999) Ionic targets for drug therapy and atrial fibrillation-induced electrical remodeling: insights from a mathematical model. *Cardiovasc. Res.* 42:477-489.
11. D'Aloia A, Faggiano P, Brentana L, Boldini A, Pedrinazzi C, Procopio R, and Dei C L (2005) Sustained torsade de pointes occurring early during oral sotalol therapy for atrial fibrillation recurrence prophylaxis in a patient without heart disease. *Int. J. Cardiol.* 105:337-339.
12. de Haan S, Greiser M, Harks E, Blaauw Y, van Hunnik A, Verheule S, Allessie M, and Schotten U (2006) AVE0118, blocker of the transient outward current (I(to)) and ultrarapid delayed rectifier current (I(Kur)), fully restores atrial contractility after cardioversion of atrial fibrillation in the goat. *Circulation* 114:1234-1242.
13. DeWitt C R and Waksman J C (2004) Pharmacology, pathophysiology and management of calcium channel blocker and beta-blocker toxicity. *Toxicol. Rev.* 23:223-238.
14. Doug M Q, Lau C P, Gao Z, Tseng G N, and Li G R (2006) Characterization of recombinant human cardiac KCNQ1/KCNE1 channels (I(Ks)) stably expressed in HEK 293 cells. *J. Membr. Biol.* 210:183-192.
15. Doostdar H, Burke M D, and Mayer R T (2000) Bioflavonoids: selective substrates and inhibitors for cytochrome P450 CYP1A and CYP1B1. *Toxicology* 144:31-38.
16. Fedida D, Orth P M, Chen J Y, Lin S, Plouvier B, Jung G, Ezrin A M, and Beatch G N (2005) The mechanism of atrial antiarrhythmic action of RSD1235. *J. Cardiovasc. Electrophysiol.* 16:1227-1238.
17. Fedida D, Wible B, Wang Z, Fermini B, Faust F, Nattel S, and Brown A M (1993) Identity of a novel delayed rectifier current from human heart with a cloned $K^+$ channel current. *Circ. Res.* 73:210-216.
18. Gao Z, Lau C P, Chiu S W, and Li G R (2004) Inhibition of ultra-rapid delayed rectifier $K^+$ current by verapamil in human atrial myocytes. *J. Mol. Cell Cardiol.* 36:257-263.
19. Gogelein H, Brendel J, Steinmeyer K, Strubing C, Picard N, Rampe D, Kopp K, Busch A E, and Bleich M (2004) Effects of the atrial antiarrhythmic drug AVE0118 on cardiac ion channels. *Naunyn Schmiedebergs Arch. Pharmacol.* 370:183-192.
20. Hashimoto N, Yamashita T, and Tsuruzoe N (2006) Tertiapin, a selective $I_{KACh}$ blocker, terminates atrial fibrillation with selective atrial effective refractory period prolongation. *Pharmacol Res.* 54:136-141.
21. Hondeghem L M (1992) Development of class III antiarrhythmic agents. *J. Cardiovasc. Pharmacol.* 20 Suppl 2:S17-S22.

22. Hsu Y L, Knio P L, and Lin C C (2004) Acacetin inhibits the proliferation of Hep G2 by blocking cell cycle progression and inducing apoptosis. *Biochem. Pharmacol.* 67:823-829.
23. Kawaii S, Tomono Y, Katase E, Ogawa K, Yano M, Koizumi M, Ito C, and Furukawa H (2000) Quantitative study of flavonoids in leaves of citrus plants. *J. Agric. Food Chem.* 48:3865-3871.
24. Kim Y M, Guzik T J, Zhang Y H, Zhang M H, Kattach H, Ratnatunga C, Pillai R, Channon K M, and Casadei B (2005) A myocardial Nox2 containing NAD(P)H oxidase contributes to oxidative stress in human atrial fibrillation. *Circ. Res.* 97:629-636.
25. Kraft C, Jenett-Siems K, Siems K, Jakupovic J, Mavi S, Bienzle U, and Eich E (2003) In vitro antiplasmodial evaluation of medicinal plants from Zimbabwe. *Phytother. Res.* 17:123-128.
26. Li G R, Feng J, Wang Z, Fermini B, and Nattel S (1996a) Adrenergic modulation of ultrarapid delayed rectifier $K^+$ current in human atrial myocytes. *Circ. Res.* 78:903-915.
27. Li G R, Feng J, Yue L, Carrier M, and Nattel S (1996b) Evidence for two components of delayed rectifier $K^+$ current in human ventricular myocytes. *Circ. Res.* 78:689-696.
28. Li G R, Lau C P, and Shrier A (2002a) Heterogeneity of sodium current in atrial vs epicardial ventricular myocytes of adult guinea pig hearts. *J. Mol. Cell Cardiol.* 34:1185-1194.
29. Li G R, Zhang M, Satin L S, and Baumgarten C M (2002b) Biphasic effects of cell volume on excitation-contraction coupling in rabbit ventricular myocytes. *Am. J. Physiol Heart Circ. Physiol* 282:H1270-H1277.
30. Liao Y H, Houghton P J, and Hoult J R (1999) Novel and known constituents from Buddleja species and their activity against leukocyte eicosanoid generation. *J. Nat. Prod.* 62:1241-1245.
31. Lip G Y and Tse H F (2007) Management of atrial fibrillation. *Lancet* 370:604-618.
32. Liu L and Nattel S (1997) Differing sympathetic and vagal effects on atrial fibrillation in dogs: role of refractoriness heterogeneity. *Am. J. Physiol* 273:H805-H816.
33. Lloyd-Jones D M, Wang T J, Leip E P, Larson M G, Levy D, Vasan R S, D'Agostino R B, Massaro J M, Beiser A, Wolf P A, and Benjamin E J (2004) Lifetime risk for development of atrial fibrillation: the Framingham Heart Study. *Circulation* 110:1042-1046.
34. Mihm M J, Yu F, Carnes C A, Reiser P J, McCarthy P M, Van Wagoner D R, and Bauer J A (2001) Impaired myofibrillar energetics and oxidative injury during human atrial fibrillation. *Circulation* 104:174-180.
35. Milberg P, Ramtin S, Monnig G, Osada N, Wasmer K, Breithardt G, Haverkamp W, and Eckardt L (2004) Comparison of the in vitro electrophysiologic and proarrhythmic effects of amiodarone and sotalol in a rabbit model of acute atrioventricular block. *J. Cardiovasc. Pharmacol.* 44:278-286.
36. Nademanee K (1992) The amiodarone odyssey. *J. Am. Coll. Cardiol.* 20:1063-1065.
37. Nattel S, hairy P, Roy D, Thibault B, Guerra P, Talajic M, and Dubuc M (2002) New approaches to atrial fibrillation management: a critical review of a rapidly evolving field. *Drugs* 62:2377-2397.
38. Nattel S and Singh B N (1999) Evolution, mechanisms, and classification of antiarrhythmic drugs: focus on class III actions. *Am. J. Cardiol.* 84:11R-19R.
39. Pan M H, Lai C S, Wang Y J, and Ho C T (2006) Acacetin suppressed LPS-induced up-expression of iNOS and COX-2 in murine macrophages and TPA-induced tumor promotion in mice. *Biochem. Pharmacol.* 72:1293-1303.
40. Pecini R, Elming H, Pedersen O D, and Torp-Pedersen C (2005) New antiarrhythmic agents for atrial fibrillation and atrial flutter. *Expert. Opin. Emerg. Drugs* 10:311-322.
41. Peukert S, Brendel J, Pirard B, Bruggemann A, Below P, Kleemann H W, Hemmerle H, and Schmidt W (2003) Identification, synthesis, and activity of novel blockers of the voltage-gated potassium channel Kv1.5. *J. Med. Chem.* 46:486-498.
42. Pirard B, Brendel J, and Peukert S (2005) The discovery of Kv1.5 blockers as a case study for the application of virtual screening approaches. *J. Chem. Inf. Model.* 45:477-485.
43. Regan C P, Wallace A A, Cresswell H K, Atkins C L, and Lynch J J, Jr. (2006) In vivo cardiac electrophysiologic effects of a novel diphenylphosphine oxide IKur blocker, (2-Isopropyl-5-methylcyclohexyl) diphenylphosphine oxide, in rat and nonhuman primate. *J. Pharmacol. Exp. Ther.* 316:727-732.
44. Roden D M (1993) Current status of class III antiarrhythmic drug therapy. *Am. J. Cardiol.* 72:44B-49B.
45. Roden D M and Anderson M E (2006) Proarrhythmia. *Handb. Exp. Pharmacol.* 73-97.
46. Salata J J, Jurkiewicz N K, Jow B, Folander K, Guinosso P J, Jr., Raynor B, Swanson R, and Fermini B (1996) $I_K$ of rabbit ventricle is composed of two currents: evidence for IKs. *Am. J. Physiol* 271:H2477-H2489.
47. Schauerte P, Scherlag B J, Pitha J, Scherlag M A, Reynolds D, Lazzara R, and Jackman W M (2000) Catheter ablation of cardiac autonomic nerves for prevention of vagal atrial fibrillation. *Circulation* 102:2774-2780.
48. Seki A, Hagiwara N, and Kasanuki H (2002) Effects of NIP-141 on K currents in human atrial myocytes. *J. Cardiovasc. Pharmacol.* 39:29-38.
49. Sharma P P, Sarma J S, and Singh B N (1999) Effects of sotalol on the circadian rhythmicity of heart rate and QT intervals with a noninvasive index of reverse-use dependency. *J. Cardiovasc. Pharmacol. Ther.* 4:15-21.
50. Shi H., Wang H, Li D, Nattel S, and Wang Z (2004) Differential alterations of receptor densities of three muscarinic acetylcholine receptor subtypes and current densities of the corresponding $K^+$ channels in canine atria with atrial fibrillation induced by experimental congestive heart failure. *Cell Physiol Biochem.* 14:31-40.
51. Singh R P, Agrawal P, Yim D, Agarwal C, and Agarwal R (2005) Acacetin inhibits cell growth and cell cycle progression, and induces apoptosis in human prostate cancer cells: structure-activity relationship with linarin and linarin acetate. *Carcinogenesis* 26:845-854.
52. Spence S, Soper K, Hoe C M, and Coleman J (1998) The heart rate-corrected QT interval of conscious beagle dogs: a formula based on analysis of covariance. *Toxicol. Sci.* 45:247-258.
53. Tang, Q, Jin, M. W., Xiang, J. Z., Dong, M. Q., Sun, H. Y., Lau, C. P., and Li, G. R. The membrane permeable calcium chelator BAPTA-AM directly blocks human ether a-go-go related gene potassium channels stably expressed in HEK 293 cells. 74, 1596-1607, 2007.
54. Tian M, Dong M Q, Chiu S W, Lau C P, and Li G R (2006) Effects of the antifungal antibiotic clotrimazole on human cardiac repolarization potassium currents. *Br. J. Pharmacol.* 147:289-297.
55. Wang T J, Larson M G, Levy D, Vasan R S, Leip E P, Wolf P A, D'Agostino R B, Murabito J M, Kannel W B, and Benjamin E J (2003) Temporal relations of atrial fibrillation and congestive heart failure and their joint influence on mortality: the Framingham Heart Study. *Circulation* 107: 2920-2925.

56. Wang Z., Fermini B, and Nattel S (1993) Sustained depolarization-induced outward current in human atrial myocytes. Evidence for a novel delayed rectifier K$^+$ current similar to Kv1.5 cloned channel currents. *Circ. Res.* 73:1061-1076.

57. Wang Z, Fermini B, and Nattel S (1994) Rapid and slow components of delayed rectifier current in human atrial myocytes. *Cardiovasc. Res.* 28:1540-1546.

58. Weissenburger J, Davy J M, and Chezalviel F (1993) Experimental models of torsades de pointes. *Fundam. Clin. Pharmacol.* 7:29-38.

59. Zhang K, Yang E B, Tang W Y, Wong K P, and Mack P (1997) Inhibition of glutathione reductase by plant polyphenols. *Biochem. Pharmacol.* 54:1047-1053.

60. Zipes D P, Mihalick M J, and Robbins G T (1974) Effects of selective vagal and stellate ganglion stimulation of atrial refractoriness. *Cardiovasc. Res.* 8:647-655.

We claim:

1. A method for treating atrial fibrillation in a patient wherein said method comprises administering to a patient having atrial fibrillation an effective amount of an isolated compound that has the following structure:

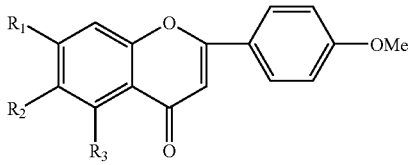

| | R$_1$ | R$_2$ | R$_3$ |
|---|---|---|---|
| A | OH | H | OH |
| A-2 | OH | H | p-methoxybenzoate |
| A-4 | H | H | H |
| A-5 | H | Cl | H |
| A-6 | H | CH$_3$ | H | or a salt thereof;
wherein the effective amount is an amount that is useful in treating atrial fibrillation and wherein the administration of the compound results in the treatment of the atrial fibrillation.

2. The method, according to claim 1, wherein said method comprises administering isolated acacetin.

3. The method, according to claim 1, wherein the patient is a human.

4. A method for inhibiting I$_{kur}$ and/or I$_{to}$ potassium channel in a patient wherein said method comprises administering to a patient who is in need of I$_{kur}$ and/or I$_{to}$ potassium channel inhibition an effective amount of an isolated compound that has the following structure:

| | R$_1$ | R$_2$ | R$_3$ |
|---|---|---|---|
| A | OH | H | OH |
| A-2 | OH | H | p-methoxybenzoate |
| A-4 | H | H | H |
| A-5 | H | Cl | H |
| A-6 | H | CH$_3$ | H | or a salt thereof;
wherein the effective amount is an amount that is useful for inhibiting I$_{kur}$ and/or I$_{to}$ potassium channel and the administration of the compound results in inhibition of I$_{kur}$ and/or I$_{to}$ potassium channel function.

5. The method, according to claim 4, wherein said method comprises administering isolated acacetin.

6. The method, according to claim 4, wherein the patient is a human.

7. The method, according to claim 1, wherein the compound is synthesized.

8. The method, according to claim 1, wherein the effective amount is from 0.001 to 100 mg/kg of body weight of the patient per day.

9. The method, according to claim 4, wherein the compound is synthesized.

10. The method, according to claim 4, wherein the effective amount is from 0.001 to 100 mg/kg of body weight of the patient per day.

* * * * *

UNITED STATES PATENT AND TRADEMARK OFFICE
CERTIFICATE OF CORRECTION

PATENT NO. : 7,816,400 B2
APPLICATION NO. : 12/039921
DATED : October 19, 2010
INVENTOR(S) : Gui-Rong Li et al.

It is certified that error appears in the above-identified patent and that said Letters Patent is hereby corrected as shown below:

Column 1,
Line 39, "antiarrhythmiic" should read --antiarrhythmic--

Column 2,
Line 31, "$T_{Kur}$" should read --$I_{Kur}$--

Column 4,
Line 22, "$T_{Kur}$" should read --$I_{Kur}$--
Line 32, "$I_{Kur}$ and $I_{to}$ prolongs" should read --$I_{Kur}$ and $I_{to}$, prolongs--

Column 13,
Line 4, "K medium" should read --$K^+$ medium--

Column 18,
Line 65-66, "10 mg kg acacetin groups, and 40% (2 of 5) of animals in the sotalol group (5 mg kg)." should read --10 mg/kg acacetin groups, and 40% (2 of 5) of animals in the sotalol group (5 mg/kg).--

Column 19,
Line 48, "all ideal compound" should read --an ideal compound--

Column 20,
Line 42, "A-02-1-11." should read --A-02-11-11.--

Column 21,
Line 3-4, "assayed by TALC" should read --assayed by TLC--

Column 22,
Line 3, "Carciovasc." should read --Cardiovasc--
Line 12, "metalbolites" should read --metabolites--

Signed and Sealed this
Twenty-fifth Day of January, 2011

David J. Kappos
*Director of the United States Patent and Trademark Office*

Column 23,
Line 1, "Knio P L" should read --Kuo PL--
Line 59, "hairy P," should read --Khairy P,--